(12) United States Patent
Sultan et al.

(10) Patent No.: US 11,301,449 B2
(45) Date of Patent: Apr. 12, 2022

(54) SYSTEMS AND NETWORKS FOR ENABLING EXERCISE EQUIPMENT TO COMMUNICATE WITH A NETWORK

(71) Applicant: Sultan Ventures LLC, Honolulu, HI (US)

(72) Inventors: Tarik Sultan, Honolulu, HI (US); Omar Sultan, Honolulu, HI (US)

(73) Assignee: SULTAN VENTURES LLC, Honolulu, HI (US)

(*) Notice: Subject to any disclaimer, the term of this patent is extended or adjusted under 35 U.S.C. 154(b) by 0 days.

(21) Appl. No.: 15/931,934

(22) Filed: May 14, 2020

(65) Prior Publication Data

US 2020/0272615 A1    Aug. 27, 2020

Related U.S. Application Data

(63) Continuation of application No. 16/147,952, filed on Oct. 1, 2018, now abandoned, which is a continuation
(Continued)

(51) Int. Cl.
*G06F 16/22*    (2019.01)
*A63B 24/00*    (2006.01)
(Continued)

(52) U.S. Cl.
CPC ...... *G06F 16/2291* (2019.01); *A63B 21/0054* (2015.10); *A63B 24/0062* (2013.01);
(Continued)

(58) Field of Classification Search
CPC ...... A63B 24/00–0087; A63B 21/0054; A63B 24/0062; A63B 24/0075; G06F 16/2291; G06F 19/00; G16H 40/67; G16H 20/30
See application file for complete search history.

(56) References Cited

U.S. PATENT DOCUMENTS 4,709,917 A  12/1987  Yang
5,089,960 A   2/1992  Sweeney
(Continued)

FOREIGN PATENT DOCUMENTS

EP    9919259 A1    6/1999
WO    9741925 A1    11/1997
WO    2005087323 A2    9/2005

OTHER PUBLICATIONS

U.S. Appl. No. 16/866,499, filed May 4, 2020.
(Continued)

*Primary Examiner* — Nyca T Nguyen
(74) *Attorney, Agent, or Firm* — Tarolli, Sundheim, Covell & Tummino LLP

(57) ABSTRACT

This disclosure provides systems, methods, and apparatus for enabling exercise by a user. In one aspect, an apparatus includes a communication unit, a user interface unit, and a processor. The processor may receive user identification data from the user via the user interface unit and retrieve data based on the user identification data from an electronic data store. The processor may use the data to generate an exercise routine and command signals may be sent to an exercise machine based on the generated exercise routine. The processor may receive exercise data from the exercise machine via the communication unit and store the exercise data in the electronic data store.

18 Claims, 10 Drawing Sheets

Related U.S. Application Data of application No. 15/855,020, filed on Dec. 27, 2017, now abandoned, which is a continuation of application No. 14/628,768, filed on Feb. 23, 2015, now Pat. No. 9,858,307, which is a continuation of application No. 13/646,309, filed on Oct. 5, 2012, now Pat. No. 8,961,371.

(60) Provisional application No. 61/545,004, filed on Oct. 7, 2011.

(51) Int. Cl.
  *A63B 21/005* (2006.01)
  *G16H 40/67* (2018.01)
  *G16H 20/30* (2018.01)
  *A63F 13/30* (2014.01)
  *A63F 13/00* (2014.01)
  *G16Z 99/00* (2019.01)

(52) U.S. Cl.
  CPC .......... *A63B 24/0075* (2013.01); *A63F 13/00* (2013.01); *A63F 13/30* (2014.09); *G16H 20/30* (2018.01); *G16H 40/67* (2018.01); *G16Z 99/00* (2019.02)

(56) References Cited

U.S. PATENT DOCUMENTS

| | | | |
|---|---|---|---|
| 5,213,555 A * | 5/1993 | Hood | A63B 71/0622 482/57 |
| 5,466,200 A | 11/1995 | Ulrich | |
| 5,474,077 A | 12/1995 | Suga | |
| 5,547,439 A | 8/1996 | Rawls | |
| 5,579,777 A | 12/1996 | Suga | |
| 5,947,868 A | 9/1999 | Dugan | |
| 6,171,218 B1 | 1/2001 | Shea | |
| 6,312,363 B1 | 11/2001 | Watterson | |
| 6,601,016 B1 | 7/2003 | Brown | |
| 6,702,719 B1 * | 3/2004 | Brown | A63B 22/00 482/8 |
| 6,746,371 B1 | 6/2004 | Brown et al. | |
| 6,749,536 B1 * | 6/2004 | Cuskaden | A63B 71/0622 482/1 |
| 6,798,798 B2 | 9/2004 | Yoshida | |
| 6,902,513 B1 * | 6/2005 | McClure | A63B 24/0006 482/4 |
| 6,921,351 B1 * | 7/2005 | Hickman | G16H 20/30 482/8 |
| 6,949,052 B2 | 9/2005 | Millington et al. | |
| 6,971,973 B2 | 12/2005 | Cohen et al. | |
| 6,997,852 B2 | 2/2006 | Watterson | |
| 7,060,006 B1 | 6/2006 | Watterson | |
| 7,166,062 B1 * | 1/2007 | Watterson | A63B 24/0084 482/1 |
| 7,166,064 B2 * | 1/2007 | Watterson | A63B 21/005 482/54 |
| 7,465,257 B1 * | 12/2008 | Morgan, Jr. | A63F 13/245 482/57 |
| 7,479,092 B2 | 1/2009 | Alessandri et al. | |
| 7,507,183 B2 | 3/2009 | Anderson et al. | |
| 7,603,255 B2 * | 10/2009 | Case, Jr | A63B 24/00 702/182 |
| 7,628,730 B1 * | 12/2009 | Watterson | A63B 22/0023 482/8 |
| 7,645,212 B2 * | 1/2010 | Ashby | A63B 24/0084 482/8 |
| 7,699,752 B1 | 4/2010 | Anderson et al. | |
| 7,736,272 B2 | 6/2010 | Martens | |
| 7,758,469 B2 * | 7/2010 | Dyer | A63B 22/001 482/4 |
| 7,833,135 B2 | 11/2010 | Radow | |
| 7,874,957 B2 * | 1/2011 | Hurwitz | F16D 65/183 482/8 |
| 7,938,752 B1 * | 5/2011 | Wang | A63B 24/0087 482/4 |
| 7,955,219 B2 * | 6/2011 | Birrell | G06Q 30/02 482/8 |
| 8,029,415 B2 * | 10/2011 | Ashby | A63B 71/0622 482/49 |
| 8,047,965 B2 * | 11/2011 | Shea | A63B 71/0697 482/8 |
| 8,103,517 B2 | 1/2012 | Hinnebusch | |
| 8,784,270 B2 | 7/2014 | Ashby et al. | |
| 8,821,350 B2 | 9/2014 | Maertz | |
| 8,892,219 B2 | 11/2014 | Pryor | |
| 8,923,994 B2 | 12/2014 | Laikari et al. | |
| 8,944,961 B2 | 2/2015 | Ainsworth et al. | |
| 9,028,368 B2 | 5/2015 | Ashby | |
| 9,174,085 B2 | 11/2015 | Foley | |
| 9,233,276 B1 | 1/2016 | Foley | |
| 9,858,307 B2 | 1/2018 | Sultan et al. | |
| 9,861,855 B2 | 1/2018 | Foley | |
| 10,022,590 B2 | 7/2018 | Foley | |
| 10,322,315 B2 | 6/2019 | Foley | |
| 10,486,026 B2 | 11/2019 | Foley | |
| 10,639,521 B2 | 5/2020 | Foley | |
| 2002/0022551 A1 * | 2/2002 | Watterson | A63B 24/0062 482/8 |
| 2002/0042328 A1 * | 4/2002 | Yoo | A63B 24/0062 482/8 |
| 2002/0045519 A1 * | 4/2002 | Watterson | A63B 22/0023 482/54 |
| 2003/0158014 A1 | 8/2003 | Valentin-Sivico | |
| 2004/0077462 A1 * | 4/2004 | Brown | A63F 13/798 482/8 |
| 2004/0102931 A1 * | 5/2004 | Ellis | A63B 24/0087 702/188 |
| 2005/0079905 A1 * | 4/2005 | Martens | A63B 24/0087 463/1 |
| 2006/0025282 A1 * | 2/2006 | Redmann | A61B 5/1112 482/8 |
| 2006/0040793 A1 * | 2/2006 | Martens | A63F 13/245 482/8 |
| 2006/0063645 A1 | 3/2006 | Chiang | |
| 2006/0184427 A1 | 8/2006 | Singh | |
| 2006/0205566 A1 * | 9/2006 | Watterson | A63B 24/0084 482/8 |
| 2007/0005395 A1 | 1/2007 | Singh | |
| 2007/0219057 A1 | 9/2007 | Fleishman | |
| 2007/0265138 A1 * | 11/2007 | Ashby | H04L 67/04 482/8 |
| 2008/0015089 A1 * | 1/2008 | Hurwitz | F16D 55/226 482/8 |
| 2008/0242514 A1 | 10/2008 | Piccionelli | |
| 2009/0111656 A1 * | 4/2009 | Sullivan | A63F 13/24 482/4 |
| 2009/0233769 A1 | 9/2009 | Pryor | |
| 2009/0258758 A1 | 10/2009 | Hickman | |
| 2010/0049470 A1 | 2/2010 | Szajnowski | |
| 2010/0062816 A1 | 3/2010 | Yu | |
| 2010/0062818 A1 * | 3/2010 | Haughay, Jr | A63F 13/212 463/7 |
| 2010/0120585 A1 | 5/2010 | Quy | |
| 2010/0160014 A1 * | 6/2010 | Galasso | A63B 24/0062 463/6 |
| 2010/0197460 A1 * | 8/2010 | Czarnecki | A63F 13/816 482/2 |
| 2010/0197461 A1 * | 8/2010 | Czarnecki | G06Q 99/00 482/2 |
| 2010/0248900 A1 * | 9/2010 | Ashby | A63B 71/0622 482/4 |
| 2010/0317489 A1 * | 12/2010 | Flaction | A63B 24/0062 482/9 |
| 2011/0003664 A1 | 1/2011 | Maertz | |
| 2011/0069613 A1 * | 3/2011 | Phillips | H04L 67/1002 370/229 |
| 2011/0086707 A1 | 4/2011 | Loveland | |
| 2011/0092337 A1 * | 4/2011 | Srinivasan | A63B 24/0062 482/8 |

(56) References Cited

U.S. PATENT DOCUMENTS

| | | | |
|---|---|---|---|
| 2011/0172059 A1* | 7/2011 | Watterson | A63B 24/0062 482/5 |
| 2011/0172060 A1* | 7/2011 | Morales | A63B 69/004 482/8 |
| 2011/0224999 A1 | 9/2011 | Baccarella-Garcia | |
| 2011/0257997 A1* | 10/2011 | Gale | G16H 10/40 705/3 |
| 2012/0040799 A1 | 2/2012 | Jaquish | |
| 2012/0162351 A1 | 6/2012 | Feldman | |
| 2012/0190505 A1 | 7/2012 | Shavit | |
| 2013/0123068 A1 | 5/2013 | Sultan | |
| 2014/0074264 A1 | 3/2014 | Anderson et al. | |
| 2015/0141202 A1 | 5/2015 | Ellis et al. | |
| 2015/0238817 A1 | 8/2015 | Watterson | |

OTHER PUBLICATIONS

U.S. Appl. No. 16/902,195, filed Jun. 15, 2020.
VR Optics, LLC, Invalidity Expert Report of R. Lee Rawls, filed in Case 1:16-cv-063920-JPO on Jul. 1, 2019, 71 pages.
Carraro et al., "The Peloton Bicycling Simulator", Proceedings of the Annual Symposium on the Virtual Reality Modeling Language, VRML, pp. 63-70, Feb. 1998.
Peloton Interactive, Inc.'s Opposition to Defendant Flywheel Sports, Inc.'s Motion to Dismiss, filed in Case 2:18-CV-00390-RWS-RSP on Dec. 24, 2018, 32 pages.
"Socially Interactive Virtual Reality Fitness", accessed Feb. 19, 2020, http://www.webracinginc.com/, 2014 Web Racing Inc.
"Socially Interactive Virtual Reality Fitness"—Products—UltraCoach, accessed Feb. 19, 2020, http://www.webracinginc.com/products_ultracoach.htm, 2014 Web Racing Inc.
"Flywheel Sports", May 20, 2010, accessed Feb. 19, 2020, http://www.flywheelsports.com/.
"Flywheel Sports"—About Us, Apr. 13, 2010, accessed Feb. 19, 2020, http://www.flywheelsports.com/about.
Jan./Feb. 1998 Issue of Bicycling Magazine (advertisement, review of CycleOps eTrainer), Verbatim Product Review from: VR Optics, LLC, Invalidity Expert Report of R. Lee Rawls, filed in Case 1:16-cv-063920-JPO on Jul. 1, 2019.
Peloton Interactive, Inc., Registration Statement (Form S-1) (Aug. 27, 2019), 206 pages.
Peloton Brochure, Peloton Interactive, Inc. (2017), Peloton Ex. 2003, 14 pages.
Bike Reviews, Peloton, Peloton Ex. 2045 (part 1), last accessed Oct. 26, 2020, 400 pages https://www.onepeloton.com/bike/reviews.
Bike Reviews, Peloton, Peloton Ex. 2045 (part 2), last accessed Oct. 26, 2020, 301 pages https://www.onepeloton.com/bike/reviews.
E-mails between Steven N. Feldman and Jeff Ginsburg, Re:IPR2019-00294, 00295, 00564: Proposed Motion for Sanctions (Dec. 31, 2019, 12:04 PM to Jan. 12, 2020, 4:56 PM), 4 pages.
ICI/Pro: Indoor Cycling 2.0, "Adding some friendly competition to your class" Nov. 9, 2011, 7 pages, https://www.indoorcycleinstructor.com/icipro-instructor-training/training-with-power/adding-some-friendly-competition-to-your-class/.
Flywheel Sports Parent Inc., Notice of Exempt Offering of Securities (Form D) (Aug. 23, 2018), 6 pages.
Reviews, Flywheel Sports, Inc., Flywheel Ex. 1042, printed Sep. 19, 2019, 38 pages, https://www.flywheelsports.com/home-bike/reviews?bvstate=pg%3A2%2Fct%3Ar.
Patent Assignment from John P. Foley to Peloton Interactive, Inc. (Form PTO-1895) (Oct. 28, 2015), 14 pages.
Peloton Interactive, Inc., Amendment No. 1 to Registration Statement (Form S-1) (Sep. 10, 2019), Flywheel Ex. 1044 (part 1), 103 pages.
Peloton Interactive, Inc., Amendment No. 1 to Registration Statement (Form S-1) (Sep. 10, 2019), Flywheel Ex. 1044 (part 2), 104 pages.

Qorix, "Peloton Bike—The Most Fulfilling Indoor Cycling Experience Ever," printed Mar. 3, 2019, 11 pages, https://www.qorix.com/peloton-bike-the-most-fulfilling-indoor-cycling-experience-ever/.
Flywheel: Stadium Cycling TM, Flywheel ex. 1020 (printed Nov. 9, 2018), 1 page, https://web.archive.org/web/20120529111518/http://www.flywheelsports.com/locations.
Flywheel@Home: Discussion Document, Confidential, Jul. 2011, Flywheel Ex. 1061, 30 pages.
Fast Company, "The World's Most Innovative Companies 2018 Honorees by Sector: Wellness," (printed Aug. 29, 2019), Peloton Ex. 2028, 6 pages, https://www.fastcompany.com/most-innovative-companies/2018/sectors/wellness.
Fast Company, "The World's 50 Most Innovative Companies 2017 Honorees by Rank," (printed Aug. 29, 2019), Peloton Ex. 2027, 10 pages, https://www.fastcompany.com/most-innovative-companies/2017/sectors/fitness.
Fast Company, "The World's 50 Most Innovative Companies 2016 Honorees by Rank," (printed Aug. 29, 2019), Peloton Ex. 2026, 16 pages, https://www.fastcompany.com/most-innovative-companies/2016/sectors/fitness.
Peloton Ex. 2025, Selection of Facebook Posts, 5 pages.
Claim Construction Chart: IPR 2019-00294, IPR 2019-00295, and IPR 2019-00564, Peloton Ex. 2053, 17 pages.
Intertek, "Internal photo of EUT", Peloton Ex. 2088, 7 pages.
Peloton Interactive, Inc., "Peloton Secures Guinness World Records TM Title for the Largest Live Cycling Class," PR Newswire (Nov. 23, 2017), https://www.prnewswire.com/news-releases/peloton-secures-guinness-world-records—title-for-the-largest-live-cycling-class-300561448.html.
E-mails between Steven N. Feldman and Jeff Ginsberg, *Peloton Interactive, Inc. v. Flywheel Sports, Inc.* (Dec. 12, 2019 3:14 PM to Dec. 14, 2019 5:54 AM).
Transcript of Conference Call Conducted on Nov. 22, 2019, *Flywheel Sports, Inc. v. Peloton Interactive, Inc.*, IPR-2019-00294, IPR 2019-00295, IPR 2019-00564, and IPR 2019-01411, Flywheel Ex. 1047, 54 pages.
Deposition of Thomas Cortese, IPR Case Nos. IPR 2019-00294, IPR 2019-00295, IPR 2019-00564, Flywheel Ex. 1035, 242 pages.
Selected Reviews of Bike Reviews, Peloton, Flywheel Ex. 1038, 67 pages, https://www.onepeloton.com/bike/reviews.
E-mail from Matt O'Conner to Michael Burlando et al., Stats Feedback (Jun. 18, 2018 7:48 PM).
E-mails between Michael Burlando and Andrey Kokoev, Teardowns (Jun. 8, 2016 9:07 PM to Jun. 13, 2016 8:07 PM).
E-mails between Tamara Odinec and Sarah Robb O'Hagan et al., notes from my weekend Peloton rides (Apr. 30, 2017 7:24 PM to Apr. 30, 2017 7:47 PM).
E-mail from Michael Burlando to Tamara Odinec et al., Peloton on The Verge (Apr. 25, 2017 5:14 PM).
E-mail from Matt O'Connor to Emma Stegman et al., Follow-ups from today's meeting on bugs/wifi (Jan. 25, 2019 3:25 PM).
E-mails Michael Burlando and Sarah Robb O'Hagan, Project Magnum (Feb. 12, 2017 11:06 PM to Mar. 15, 2017 9:51 AM).
E-mails between Matthew C. Phillips and Jeff Ginsberg et al., IPR2019-00294, IPR-2019-00295, IPR2019-00564—Petitions to Correct Inventorship (Oct. 25, 2019 2:11 PM to Dec. 6, 2019 12:37 PM).
E-mails between Sarah Robb O'Hagan, Julia Takeda, and Sylvia Calos et al., Project Magnum (Jan. 12, 2017 4:40 PM to Jan. 14, 2020 2:30 PM).
Redacted Claim Chart for IPR2019-00294, IPR 2019-00295, and IPR2019-00564, Peloton Ex. 2054, 34 pages.
Transcript of Conference Call Conducted on Nov. 22, 2019, Planet Depos, *Flywheel Sports, Inc. v. Peloton Interactive, Inc.*, IPR-2019-00294, IPR 2019-00295, IPR 2019-00564, and IPR 2019-01411, Flywheel Ex. 1047, 54 pages.
Project Magnum (as of Jan. 25, 2017), Flywheel Ex. 2097, 16 pages.
Project Magnum (as of Jan. 25, 2017) (Redacted), Flywheel Ex. 1055, 14 pages.

(56) References Cited

OTHER PUBLICATIONS

Peloton Interactive, Inc.'s Disclosure of Asserted Claims and Infringement Contentions, *Peloton Interactive, Inc.* v *Flywheel Sports, Inc.*, Civil Action No. 218-CV-00390-RWS-RSP (2019), Peloton Ex. 2048 (part 1), 130 pages.
Peloton Interactive, Inc.'s Disclosure of Asserted Claims and Infringement Contentions, *Peloton Interactive, Inc.* v *Flywheel Sports, Inc.* Infringement Chart, Civil Action No. 218-CV-00390-RWS-RSP (2019), Peloton Ex. 2048 (part 2), 135 pages.
"Flywheel Sports," Screen captures at 1:08 and 1:25 of 3:56 from Mirror/Mirror, Episode 24, Season 4, Segment 4, The Live Well Network, Flywheel Ex. 1023, 1 page, http://livewellnetwork.com/Mirror-Mirror/episodes/Flywheel-Sports/8577947.
Maureen Farrell, "Peloton's Financing Round Values Stationary-Bike Maker at $4.15 Billion", Wall Street Journal, Business, Aug. 3, 2018.
Jonathan C. Miller, "Fitness Insider FitTech of the Year 2014 The Peloton Bike", Fitness Insider, Dec. 24, 2014.
The Fitnessista, "Peloton Bike Review: Is It Worth the Money?", Sep. 17, 2018.
Elizabeth Fournier, "Cycling Startup Peloton Files for IPO Amid Mixed Trading Debuts by Tech Firms", Los Angeles Times, Jun. 5, 2019.
Jason Gay, "I Hated Spinning. Then I Spun", The Wall Street Journal, Tech, Gear & Gadgets, Feb. 16, 2017.
Megan Geuss, "Group Video Chat Showdown: Google Hangouts and AnyMeeting Come Out on Top", PC World, Nov. 7, 2011.
Lauren Glassberg, "Flatiron Studio Takes Spin Class Up a Notch", Mar. 11, 2010, NY WABC News.
Lauren Goode, "My two-month ride with Peloton, the Cultish, Internet-Connected Fitness Bike", Apr. 26, 2017, The Verge, https://www.theverge.com/2017/4/25/15408338/bike-peloton-review-indoor-cycle-live-streaming-cycling.
Tom Huddleston, Jr., "How Peloton Exercise Bikes Became a $4 Billion Fitness Start-Up With a Cult Following", Feb. 12, 2019, CNBC The Upstarts, https://www.cnbc.com/2019/02/12/how-peloton-exercise-bikes-and-streaming-gained-a-cult-following.html.
Jennifer Jolly, "Upgrade Your Workouts with New Fitness Tech", USA Today, Tech, Apr. 27, 2015 https://www.usatoday.com/story/tech/personal/2015/04/27/fitness-tech/26444947/.
Kiel Porter, "Flywheel Sports Taken Over by Lender, Exploring Sale", Bloomberg, Deals, May 12, 2019 https://www.bloomberg.com/news/articles/2019-05-12/flywheel-sports-taken-over-by-lender-and-is-said-to-explore-sale.
Leena Rao, "Skype Teams Up with Citrix to Bring GoToMeeting Web Conferencing to Business Offerings", TechCrunch, Mar. 1, 2011.
Katherine Rosman, "The Latest Spin in Studio Cycling: Anti-Sweat Bikes", The Wall Street Journal, Life & Culture, Oct. 18, 2011.
Hannah Sutker, "Meet Peloton, the Next Big Indoor Bike", BTRToday, Theme Week, Jan. 25, 2016.
Nick Sortal, "Flywheel Brings High-Tech Cycling to South Florida", SunSentinel.com, Article Collections, Apr. 16, 2011.
Declaration of Kevin M. Arst; IPR Case No. IPR2019-00294, 142 pages.
Declaration of Dr. Bryan Bergeron; IPR Case No. IPR2019-00294, 131 pages.
Dr. Bryan Bergeron Declaration in Support of Defendants Indefiniteness Claim Construction Position Relating to the Term "Substantially in Real-Time", Civil Action No. 2:18-CV-00390-RWS-RSP, dated Nov. 4, 2019, 8 pages.
Oral and Videotaped Deposition of Dr. Bryan Bergeron, Civil Action No. 2:18-CV-00390-RWS-RSP, dated Nov. 12, 2019, 133 pages.
Transcript of Videotaped Deposition of Dr. Bryan Bergeron commencing Jul. 26, 2019, IPR2019-00294, 200 pages.
Declaration of Tom Cortese; IPR Case No. IPR2019-00294, IPR2019-00295, IPR2019-00564, 47 pages.

Xu, Yang, et al. "Video telephony for end-consumers: measurement study of Google+, iChat, and Skype." Proceedings of the 2012 Internet Measurement Conference. 2012.
Elizabeth Woyke, "Facebook, Google Battle to be Video-Calling Home Base", Forbes, Technology, Jul. 6, 2011.
Troy Wolverton, "Peloton says only 0.65% of its subscribers cancel each month. Here's why customer-retention experts think that number 'doesn't pass the smell test.'", Business Insider, Aug. 31, 2019.
Jay Willis, "The Peloton Bike Brings the Beautiful Hell of Spin Class to Your Own Home", GQ Magazine, Fitness, Jun. 7, 2017 https://www.gq.com/story/peloton-bike-review.
Jamie Ducharme, "Peloton, The Portable Fitness Class", Time, Feb. 18, 2019 http://time.com/collection/genius-companies-2018/5412650/peloton/.
Victoria Song, "Peloton Bike Review and Rating", PCMag, Sep. 11, 2018 https://www.pcmag.com/review/363465/peloton-bike.
Catherine Saint Louis, "In New York, a Rivalry Shifts Into High Gear", The New York Times, Fashion & Style, published Oct. 8, 2010, printed Oct. 10, 2010.
Mark Prigg, "Peloton's hi-tech $2,000 spin bike really could change your life" DailyMail.com, Science Tech, Apr. 25, 2016, https://www.dailymail.co.uk/sciencetech/article-3552959/The-hi-tech-2-000-spin-bike-really-change-life.html.
Declaration of Matthew C. Phillips; IPR Case No. IPR2019-00294, IPR2019-00295, IPR2019-00564, 3 pages.
Complaint for Patent Infringement, dated Sep. 12, 2018, for Civil Action No. 2:18-cv-00390-RWS-RSP, 24 pages.
Declaration of Mark Ehsani, Ph D., for IPR Case No. IPR2019-00294, 73 pages.
Second Declaration of Mark Ehsani, Ph.D.; for IPR Case No. IPR2019-00294, IPR2019-00295, IPR2019-00564, 55 pages.
Declaration of Kevin B, Laurence; IPR Case No. IPR2019-00294, IPR2019-00295, IPR2019-00564, 7 pages.
Declaration of Sarah Robb O'Hagan; Civil Action No. 2:18-cv-00390-RWS-RSP, 4 pages.
Declaration of Mark Ehsani, Ph.D. regarding Claim Construction, for Civil Action No. 2:18-cv-00390-RWS-RSP, 54 pages.
Videotaped Deposition of Mark Ehsani, Ph.D. dated Nov. 14, 2019, for Civil Action No. 2:18-cv-00390-RWS-RSP, 135 pages.
Videotaped Deposition of Mark Ehsani, Ph.D. dated Nov. 8, 2019, for IPR Case No. IPR2019-00294, IPR2019-00295, IPR2019-00564, 278 pages.
Petition for Inter Parties Review; IPR Case No. IPR2019-00294, 79 pages.
Paisley + Sparrow, Fitness, Life, Mar. 18, 2019, "Is the Peloton Worth it? My Peloton Bike Review 2019" https://paisleyandsparrow.com/is-the-peloton-bike-worth-it-my-peloton-review/.
Larry Olmsted, "The Best Home Workout & Fitness Machine: Peloton Review", Forbes, Nov. 2, 2016.
Complaint for Patent Infringement,Trademark Infringement, Trade Dress Infringement, Trademark and Trade Dress Dilution, Trade Libel,False Advertising, and Unfair Business Practices for Case 1:19-cv-01903-UNA, filed Oct. 8, 2019, 47 pages.
Lu, Yue, et al. "Measurement study of multi-party video conferencing." International Conference on Research in Networking. Springer, Berlin, Heidelberg, 2010.
Joint Claim Construction and Prehearing Statement for Civil Action No. 2:18-CV-00390-RWS-RSP, filed Nov. 4, 2019, 11 pages.
Cardio Motivation: Hugh Jackman's Peloton Bike PR Will Make You Want To Cycle, Men's Health, Singapore, Mar. 12, 2018 https://www.menshealth.com.sg/fitness/cardio-hugh-jackman-peloton-bike-pr-motivation-make-you-want-to-cycle/.
Peloton Bike, Best Cardio Machine; Men's Health, May 2015.
Declaration of Kevin Jeffay, Ph.D; IPR Case No. IPR2020-01541, 149 pages.
Petition for Inter Parties Review of Claims 1-20 of U.S. Pat. No. 10,486,026; IPR Case No. IPR2020-01541, 91 pages.
Declaration of Kevin Jeffay, Ph.D; IPR Case No. IPR2020-01187, 156 pages.
Petition for Inter Parties Review of Claims 1-20 of U.S. Pat. No. 10,022,590; IPR Case No. IPR2020-01187, 90 pages.

(56) References Cited

OTHER PUBLICATIONS

Declaration of Kevin M. Arst; IPR Case No. IPR2019-00295, 141 pages.
Declaration of Dr. Bryan Bergeron; IPR Case No. IPR2019-00295, 146 pages.
File History of U.S. Appl. No. 14/930,398, issued as U.S. Pat. No. 9,233,276 on Jan. 12, 2016, 106 pages.
Petition for Inter Parties Review; IPR Case No. IPR2019-00295, 78 pages.
File History of U.S. Appl. No. 16/412,327, issued as U.S. Pat. No. 10,486,026 on Nov. 26, 2019, 231 pages.
File History of U.S. Appl. No. 16/036,894, issued as U.S. Pat. No. 10,322,315 on Jun. 18, 2019, 328 pages.
File History of U.S. Appl. No. 15/865,206, issued as U.S. Pat. No. 10,022,590 on Jul. 17, 2018, 160 pages.
File History of U.S. Appl. No. 14/992,032, issued as U.S. Pat. No. 9,861,855 on Jan. 9, 2018, 336 pages.
File History of U.S. Appl. No. 14/930,398, issued as U.S. Pat. No. 9,233,276 on Jan. 12, 2016, 186 pages.
Petition for Inter Parties Review of Claims 1-20 of U.S. Pat. No. 10,322,315; IPR Case No. IPR2020-01186, 85 pages.
Declaration of Kevin Jeffay, Ph.D; IPR Case No. IPR2020-01186, 145 pages.
Jeff Carlson, "The iPad 2 Pocket Guide", Echelon Ex. 1014, 2011, 265 pages.
Library of Congress Record for Jeff Carlson, The iPad 2 pocket guide, LCCN: 2011282595.
Amended Complaint for Patent Infringement, Trademark Infringement, Trade Dress Infringement, Trademark and Trade Dress Dilution, Trade Libel, False Advertising, and Unfair Business Practices for C.A. No. 19-1903 (RGA), Jan. 10, 2020, 54 pages.
P.R. 4-5(d) Joint Claim Construction Chart, Civil Action No. 2-18-CV-00390-RWS-RSP, filed Dec. 20, 2019, 46 pages.
Petition for Inter Parties Review; IPR Case No. IPR2019-00564, 81 pages.
Declaration of Dr. Bryan Bergeron; IPR Case No. IPR2019-00564, 150 pages.
Declaration of Mark Ehsani, Ph D.; IPR Case No. IPR2019-00564, 73 pages.
Declaration of Kevin M. Arst; IPR Case No. IPR2019-00564, 141 pages.
File History of U.S. Appl. No. 14/992,032, issued as U.S. Pat. No. 9,861,855 on Jan. 9, 2018, 267 pages.
Flywheel Sports webpage, 2012, printed Dec. 14, 2018, last accessed Oct. 21, 2020 https://web.archive.org/web/20120529111518/http://www.flywheelsports.com/locations.
Flywheel Sports performance metrics, 2012, printed Dec. 14, 2018, last accessed Oct. 21, 2020 http://web.archive.org/web/20120128121139/http://new-york.flywheelsports.com:80/performance-metrics.
Flywheel Sports, Best Indoor Cycling, locations, printed Dec. 10, 2018, last accessed Oct. 21, 2020 http://web.archive.org/web/20120106083132/http://www.flywheelsports.com:80/locations.

Netathlon, Virtual Athletic Training & Competition user interface manual, Fit Centric Technologies, 40 pages https://web.archive.org/web/20100331050623/http://www.riderunrow.com:80/pdf/NA%201.0%20User%20Guide.PDF.
Michael Marriott, "Your Shot, He Said, Distantly", The New York Times, Business Day Technology, Global Edition, Aug. 26, 2004 http://www.nytimes.com/2004/08/26/technology/your-shot-he-said-distantly.html.
Florian Mueller, "The Design of Networked Exertion Games", Journal of Virtual Reality and Broadcasting, vol. 5 (2008), No. 13, 14 pages.
Affidavit of Christopher Butler dated Dec. 17, 2018 and Exhibit A re: Internet Archive, 101 pages.
File History of U.S. Appl. No. 16/036,894, issued as U.S. Pat. No. 10,322,315 on Jun. 18, 2019, 300 pages.
File History of U.S. Appl. No. 15/865,206, issued as U.S. Pat. No. 10,022,590 on Jul. 17, 2018, 126 pages.
Petition for Inter Parties Review; IPR Case No. IPR2019-01411, 85 pages.
Declaration of Dr. Bryan Bergeron; IPR Case No. IPR2019-01411, 169 pages.
Peloton Interactive, Inc.'s Disclosure of Asserted Claims and Infringement Contentions for U.S. Pat. No. 10,322,315, for Civil Action No. 2:18-CV-00390-RWS-RSP, dated Jul. 26, 2019, 5 pages.
Declaration of Ruth Zukerman; IPR Case No. IPR2019-00564, 27 pages.
Comparison of Watterson patent application (U.S. Pat. No. 6,997,852) completed Jul. 15, 2019 at 4:05pm, 55 pages.
Flywheel Sports, Inc.'s Invalidity Contentions for Civil Action No. 2:18-CV-00390-RWS-RSP, dated Sep. 10, 2019, 133 pages.
Leah Zerbe, Aug. 26, 2016, "Peleton Bike: The Most Addictive Piece of Exercise Equipment on the Planet", Dr. Axe Food is Medicine, 5 pages.
File History of U.S. Appl. No. 16/412,327, issued as U.S. Pat. No. 10,486,026 on Nov. 26, 2019, 182 pages.
John Abella, "The Absolute Beginner's Guide to Peloton", Dec. 28, 2017, 11 pages https://medium.com/@JohnA/the-absolute-beginners-guide-to-peloton-eb0a42933ce3.
Riyad Alshammari, "An Investigation on the Identification of VoIP traffic: Case Study on Gtalk and Skype" 2010 International Conference on Network and Service Management. IEEE, 2010.
Hillary Bennetts, "I Tried It: The Peloton Bike", Purposeful Plate Nutrition, Jun. 2, 2017.
Dario Bonfiglio, "Detailed analysis of skype traffic." IEEE Transactions on Multimedia vol. 11, No. 1, Jan. 2008, pp. 117-127.
Alexie Brue, Good Sweat, "Soulcycle vs. Flywheel: A Comparison Shop and Spin", Feb. 22, 2010, Well Good.
Jon Callaghan, "Peloton Arrives in Palo Alto", Sep. 15, 2016, True Ventures.
Lisa Eadicicco, "Working Out is Hard. Streaming Just Might Make it Easier", Peloton and Streaming Fitness Tech Will Redefine Exercise, written May 31, 2018, Time, Jun. 11, 2018 issue https://time.com/5296639/streaming-exercise-peloton-workout/.

\* cited by examiner

SYSTEMS AND NETWORKS FOR ENABLING EXERCISE EQUIPMENT TO COMMUNICATE WITH A NETWORK

CROSS-REFERENCE TO RELATED APPLICATIONS

This application is a Continuation under 35 U.S.C. § 120 of U.S. patent application Ser. No. 16/147,952, filed Oct. 1, 2018, which is a Continuation under 35 U.S.C. § 120 of U.S. patent application Ser. No. 15/855,020, filed Dec. 27, 2017, which is a Continuation of U.S. Pat. No. 9,858,307, filed Feb. 23, 2015, which is a Continuation under 35 U.S.C. § 120 of U.S. Pat. No. 8,961,371, filed on Oct. 5, 2012, which claims priority under 35 U.S.C. § 119(e) to U.S. Provisional Patent Application No. 61/545,004, entitled "SYSTEMS AND METHODS FOR ENABLING EXERCISE EQUIPMENT TO COMMUNICATE WITH A NETWORK" and filed on Oct. 7, 2011, the entire contents of all of which disclosures are herewith incorporated by reference.

BACKGROUND

Field

This disclosure generally relates to networked exercise machines and more particularly to improved methods and systems for enabling exercise equipment to store energy, collect user data, and transmit such data over a network.

Description of the Related Art

Many gymnasiums provide customers with access to aerobic and/or lifting exercise equipment. Generally, customers that wish to keep track of their physical fitness and develop a custom exercise routine must either manually enter information related to their physical activity into a computer or hire a personal trainer. Both options are inefficient, time consuming, and important data may be lost due to inattention, or simply is not captured at all with conventional equipment. What are needed are systems and methods that solve these problems.

SUMMARY OF THE INVENTION

Various implementations of systems, methods and devices within the scope of the appended claims each have several aspects, no single one of which is solely responsible for the desirable attributes described herein. Without limiting the scope of the appended claims, some prominent features are described herein.

One aspect of the disclosure provides an apparatus to enable exercise by a user. The apparatus comprises a communication unit configured to receive and transmit data over a network. The apparatus further comprises a user interface unit configured to receive input from and present information to the user. The apparatus further comprises a processor in communication with the communication unit and the user interface unit. The processor may be configured to receive, via the user interface unit, user identification data from the user, where the user identification data may be transmitted by the communication unit to an electronic data store over the network. The processor may be further configured to receive, via the communication unit, user data from the electronic data store in response to transmission of the user identification data, where the user data may comprise user health data and at least one application. The processor may be further configured to identify a first application selected by the user via the user interface unit. The processor may be further configured to generate an exercise routine based on execution of the first application. The processor may be further configured to generate command signals based on the generated exercise routine, where the command signals may be transmitted to an exercise machine via the communication unit. The processor may be further configured to receive, via the communication unit, exercise data from the exercise machine in response to transmission of the command signals. The processor may be further configured to transmit, via the communication unit, the exercise data in the electronic data store.

Another aspect of the disclosure provides a system for enabling competitive exercising. The system comprises a server device configured to relay data over a network. The system further comprises a first network device in communication with the server device via the network. The first network device may be configured to execute a competition program in response to a request by a first user. The first network device may be further configured to identify a second user that the server device indicates is available and that is selected by the first user. The first network device may be further configured to identify an application selected by the first user. The first network device may be further configured to generate an exercise routine based on execution of the application. The first network device may be further configured to transmit command signals to a first exercise machine. The first network device may be further configured to receive first user exercise data from the first exercise machine. The first network device may be further configured to transmit the first user exercise data to the server device. The first network device may be further configured to receive second user exercise data from the server device. The first network device may be further configured to display the second user exercise data. The system further comprises a second network device in communication with the server device via the network. The second network device may be configured to transmit data to the server device indicating that the second user is available. The second network device may be further configured to receive the command signals from the first network device in response to a selection of the second user by the first user. The second network device may be further configured to transmit the command signals to a second exercise machine. The second network device may be further configured to receive the second user exercise data from the second exercise machine the second network device may be further configured to transmit the second user exercise data to the server device. The second network device may be further configured to receive the first user exercise data from the server device. The second network device may be further configured to display the first user exercise data.

Another aspect of the disclosure provides a system for providing charging power. The system comprises an exercise machine configured to generate power based on a use of the exercise machine by a user. The exercise machine may be further configured to track an amount of power generated by the exercise machine. The exercise machine may be further configured to transmit the power generated by the exercise machine to an energy storage device. The system further comprises an energy allocation controller in communication with the exercise machine. The energy allocation controller may be configured to receive a message from the exercise machine, where the message may comprise an indication of the amount of power generated by the exercise machine and an identity of the user. The energy allocation controller may be further configured to determine a percentage value associated with the user, where the percentage value may be based on a percentage of a total amount of power stored in the energy storage device that is contributed by the exercise machine. The energy allocation controller may be further configured to transmit command signals to the energy storage device, where the command signals may instruct the energy storage device to transmit a percentage of the total amount of power stored in the energy storage device to a charging station associated with the user. The percentage of the total amount of power may be based on the percentage value.

BRIEF DESCRIPTION OF THE DRAWINGS

Features and aspects, and advantage of the embodiments of the invention are described in detail below with reference to the drawings of various embodiments, which are intended to illustrate and not to limit the invention. The drawings include the following figures in which.

DETAILED DESCRIPTION OF THE EMBODIMENT

Figure 1A:
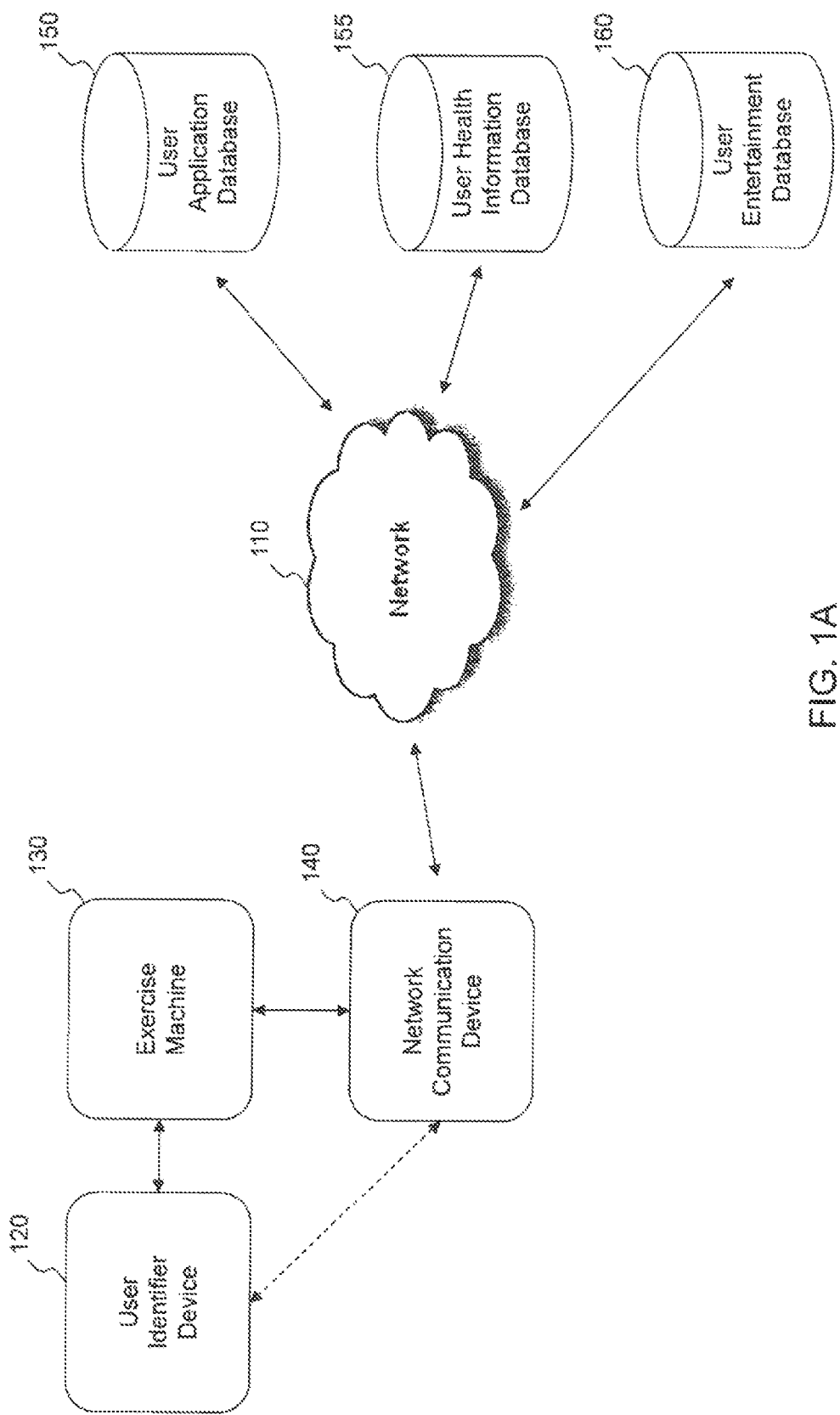
FIG. 1A is a block diagram depicting an embodiment of an exercise machine that is connected to a network via a network communication device.

In general, customers of gymnasiums and people who would like to stay fit may track data relating to their workout in order to improve their performance. Exercise machines, specifically aerobic machines like ellipticals and treadmills, can detect a user's heart rate, the number of calories burned, and the distance traveled. However, if a user wished to record such data, the user would have to manually enter it into his or her paper records, handheld device, computer, or other database. In fact, exercise machines that allow a user to lift weights do not calculate any workout-related data. This means that a user would have to remember and later record how much weight was lifted, how many reps were done, and how many sets were completed. Even if the user did remember to store the workout-related data, the user would still need to retrieve the data manually to determine how best to structure a future exercise routine in order to maximize performance. Accordingly, there is a need for a system that can automatically calculate workout-related data, store it at a central repository, and retrieve it at a later time to improve a user's workout performance.

In addition, many aerobic exercise machines may have pre-selected programs available for a user to select and run. For example, on an elliptical, a user may be able to select a program that simulates running on rolling hills, running uphill, or running downhill. However, these pre-selected programs only give a limited number of options to the users. The programs may allow a user to select distances to run in specified increments or an exact time to run in specified increments. Both male and female persons frequent gymnasiums or purchase exercise machines and are of all ages, heights, weights, and ethnicities. Accordingly, there is a need for a system that can execute any application of the user's choosing to ensure that the user is working out efficiently.

Accordingly, the systems and methods described herein can be used to improve workout performance. In an embodiment, the system automatically collects, stores, and retrieves a user's health and/or workout data. For example, a user's health and/or workout data can include, without limitation, age, sex, geographical location, ethnicity, the number of reps done, the number of sets completed, the time taken between reps, the time taken between sets, the amount of weight lifted, distance run, speed, number of calories consumed, number of calories burned, heart rate, wattage produced, exercise equipment used, which exercise equipment is used the roost, winch exercise equipment is used the least, the time of day the workout took place, the time of the year the workout took place, preexisting conditions, prior injuries, muscle gained, fat lost, or the like.

In further embodiments, the collected speed and/or heart rate data can be broken into time intervals such that a user could view his or her speed data or heart rate data between certain points during the exercise. Time intervals could be in the milliseconds, seconds, minutes, or the like. A user may find such information helpful in determining the time of peak performance or optimal ways to work out. In addition, such information can be useful to advertisers that produce advertisements for the system as described below.

In some embodiments, the number of calories consumed can be entered manually by the user via a website or other portal accessible via a network. In other embodiments, the number of calories consumed can be collected by a user's portable device, such as a cell phone, a smart phone, an iPod, an iPad, a tablet, a camera, a PDA, a laptop, or the like. For example, the user could input the number of calories consumed by verbally communicating with the user's portable device as to what food was eaten. Likewise, a portable device equipped with a near field communication (NFC) chip could be used to purchase food products to be consumed by the user. The portable device could then estimate the number of calories consumed by the user based on the food products purchased. Furthermore, a portable device could be used to take a photograph of a food product to be consumed by the user. The portable device can then compare the photograph taken with known food products in order to determine the type of food consumed and the number of calories consumed. The portable device can access a network such as the Internet in order to identify the food product in a given photograph.

In an embodiment, a user's health and/or workout data can be collected from the user directly through a website or other portal accessible via a network. The user's health and/or workout data can then be stored in a central repository. Alternatively or in conjunction, the user's health and/or workout data can be stored in a personal device, like a cell phone, a smart phone, a tablet, a PDA, a camera, a flash drive, a memory card, an optical disc, a laptop, a desktop, or the like. In another embodiment, the user's health and/or workout data can be collected from a handheld device associated with the user. The handheld device can then transmit the health and/or workout data to the central repository. In another embodiment, the user's health and/or workout data can be collected from an exercise machine in use by the user. To collect health data such as heart rate or the like, sensors can be attached to the handles or to a clip that the user can wear, or the data can be collected directly from the exercise machine in use (e.g., via sensors attached to, embedded within, or otherwise located within the exercise machine, etc.). The sensors may communicate measurements that are captured via a wired or wireless connection. When the user is exercising on an aerobic machine, sensors that can detect the number of revolutions can be used to collect workout data such as distance run, speed, calories burned, or the like. Such sensors can be located externally to the aerobic machine (e.g., attached to the aerobic machine) or can be embedded within the aerobic machine. When the user is exercising on a lifting machine, sensors like, without limitation, pressure sensors, accelerometers, or tension sensors, can be used to collect workout data such as the number of reps, the number of sets, the amount of weight lifted, wattage produced, or the like. Such sensors can be located externally to the lifting machine (e.g., attached to the lifting machine) or can be embedded within the lifting machine (e.g., within the structure of the lifting machine, within the weights of the lifting machine, etc.). When the user is exercising using medicine balls, dumbbells, other free weights, or the like, sensors like, without limitation, pressure sensors, accelerometers, or tension sensors, can be used to collect workout data such as the number of reps, the number of sets, the amount of weight lifted, wattage produced, or the like. Such sensors can be located externally to the medicine balls, dumbbells, other free weights (e.g., attached to the medicine balls, dumbbells other free weights) or can be embedded within the medicine balls, dumbbells, other free weights. The exercise machine can transmit the health and/or workout data through a network to the central repository.

The health and/or workout data stored in the central repository can also be accessible by the user via a network connection. For example, the user can view the data at any time in a web browser. The data can be organized in charts, graphs, or any other visual representation. In addition, the data can be explained audibly for the visual impaired.

To improve the efficiency of a user's workout, the system can execute any application or applications of the user's choosing. In an embodiment, the application or applications executed can utilize the user's health and/or workout data retrieved from the central repository to send commands to an exercise machine instructing the machine how to perform. An application can use some or all of the available user health and/or workout data. In another embodiment, the application or applications can extract health and/or workout data collected by an exercise machine to track a user's progress. In an additional embodiment, the application or applications can serve to entertain the user as the user performs his or her workout. In another embodiment, the application or applications can allow for at least two users to compete against one another. The application or applications can display each user's progress to the other such that at least two users could compete against one another even if there is a geographical distance separating the at least two users.

FIG. 1A is a diagram illustrating an embodiment of an exercise machine 130 in communication with a network 110. Exercise machine 130 can be an aerobic machine, lifting machine, or any other type of exercise equipment. For example, exercise machine 130 can include, without limitation, a treadmill, an elliptical, an exercise bicycle, a controlled weight machine, bench presses, or the like. Exercise machine 130 is not limited to fixed apparatuses, and can include medicine balls, dumbbells, other free weights, or the like. Network 110 can be a LAN, WAN, or the Internet Exercise machine 130 can communicate with network 110 through network communication device 140, which can be embodied as a computer system in an embodiment, exercise machine 130 is physically attached to network communication device 140, either directly or indirectly via an intermediary module. In another embodiment, exercise machine 130 is in wireless communication with network communication device 140. For example, network communication device 140 can communicate with exercise machine 130 via the 802.11 standard, the 802.15.4 standard, radio-frequency identification (RFID), NFC, Bluetooth, or any other wireless communication means.

Network communication device 140 can retrieve health and/or workout data collected from exercise machine 130 and transmit such data to user health information database 155 for storage. Likewise, network communication device 140 can retrieve health and/or workout data stored in user health information database 155. Network communication device 140 can also retrieve at least one application acquired by a user and stored in user application database 150. The at least one application retrieved from user application database 150 and health and or workout data retrieved from user health information database 155 can be used by network communication device 140 to send command signals to exercise machine 130.

Network communication device 140 can also retrieve entertainment data stored in user entertainment database 160. Entertainment data can include, without limitation, music, movies, TV shows, books, magazines, games, crosswords, or other types of media. Network communication device 140 can transmit this entertainment data to exercise machine 130 to display or play such content.

User identifier device 120 is a module that can be used to uniquely identify an individual. A user may wish to log into exercise machine 130 such that the user can load his or her own applications, generate a customized exercise routine, and/or allow the system to record and store the user's health and/or workout data. User identifier device 120 can be any device that can uniquely identify an individual, including, without limitation, a biosensor, a fingerprint scanner, a card reader, a phone dock, a voice recognition module, a visual portal with a login screen, a retina scanner, a facial recognition module, or the like.

Data from user application database 150, user health information database 155, and/or user entertainment database 160 can be accessible by using e uniquely identifiable key. This key can be based off of data acquired by user identifier device 120 regarding the user. In an embodiment, user identifier device 120 can generate this key and transmit it to exercise machine 130 and/or network communication device 140. In another embodiment, user identifier device 120 can send data acquired from the user to exercise machine and/or network communication device 140, and network communication device 140 can generate the key.

In some embodiments, one or more of the databases described above can be implemented using a relational database, such as DB2, Sybase, MySQL, Oracle, CodeBase, and Microsoft® SQL Server as well at other types of database such as a flat-file database, an entity relationship database, and object-oriented database, and/or a record-based database. The databases described above can be stored in a central repository or in different locations. The databases can be housed in a server apparatus or in a personal device, like a cell phone, a smart phone, a PDA, a tablet, a laptop, a desktop, a camera, a flash drive, a memory card, an optical disc, or the like. Note that while FIG. 1A depicts three databases, other embodiments can include more or less databases depending on the type of data a user may request. As is described herein, network communication device 140 can run operating system software and a user can request data through a web-enabled user access point. Accordingly, a user can request any data available through network 110 and supported by the operating system software.

Figure 1B:
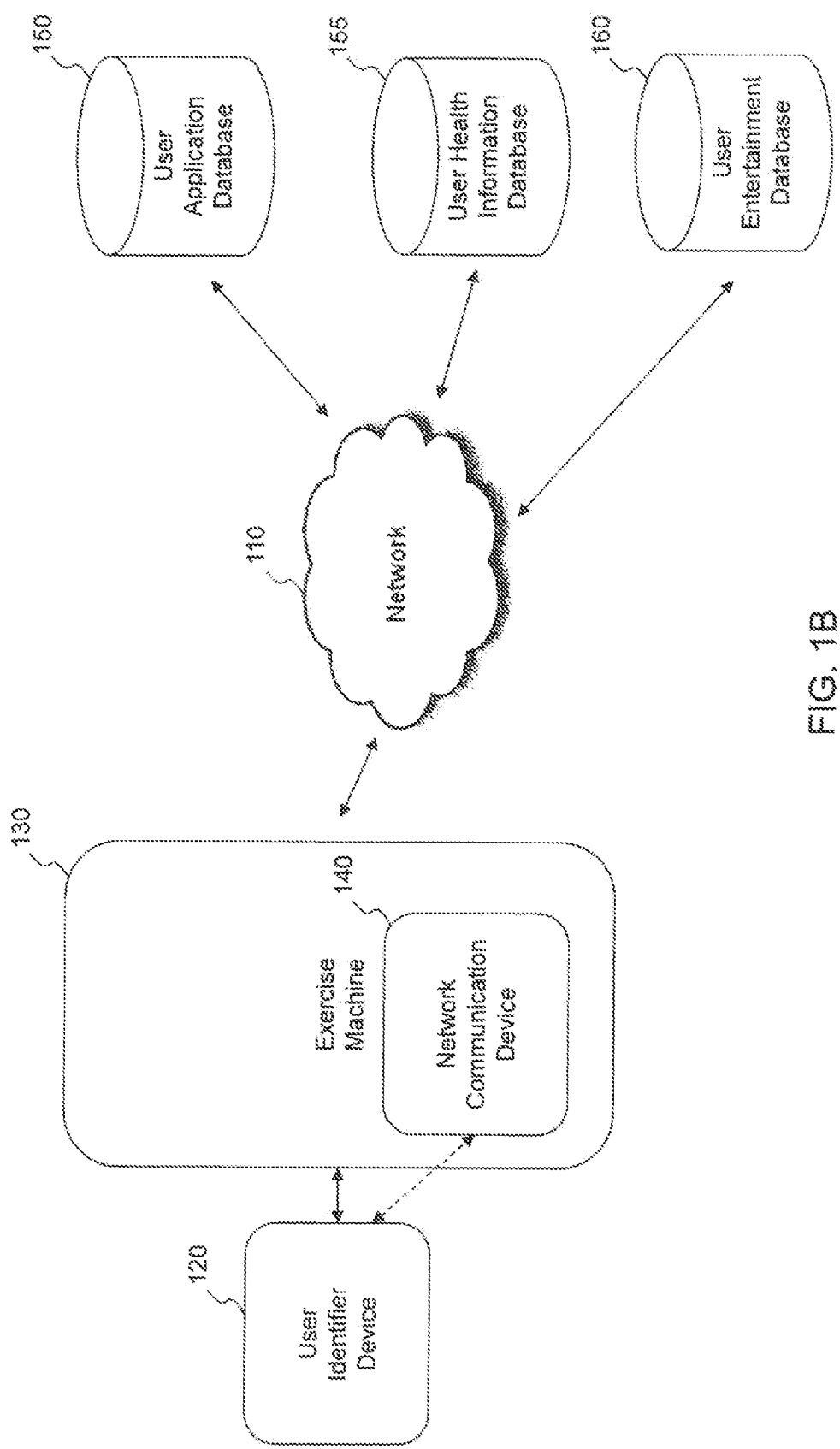
FIG. 1B is a block diagram depicting an embodiment of an exercise machine that includes a network communication device for communication with a network.

FIG. 1B is a diagram illustrating an embodiment of exercise machine 130 in which network communication device 140 is embedded in exercise machine 130. While embedded in exercise machine 130, network communication device 140 can function as described above with respect to FIG. 1A. Likewise, the communications between user identifier device 120 and exercise machine 130 and/or network communication device 140 remain as described above with respect to FIG. 1A. Network communication 140 can still be in communication with network 110 in order to retrieve data stored in user application database 150, user health information database 155, and/or user entertainment database 160.

Figure 1C:
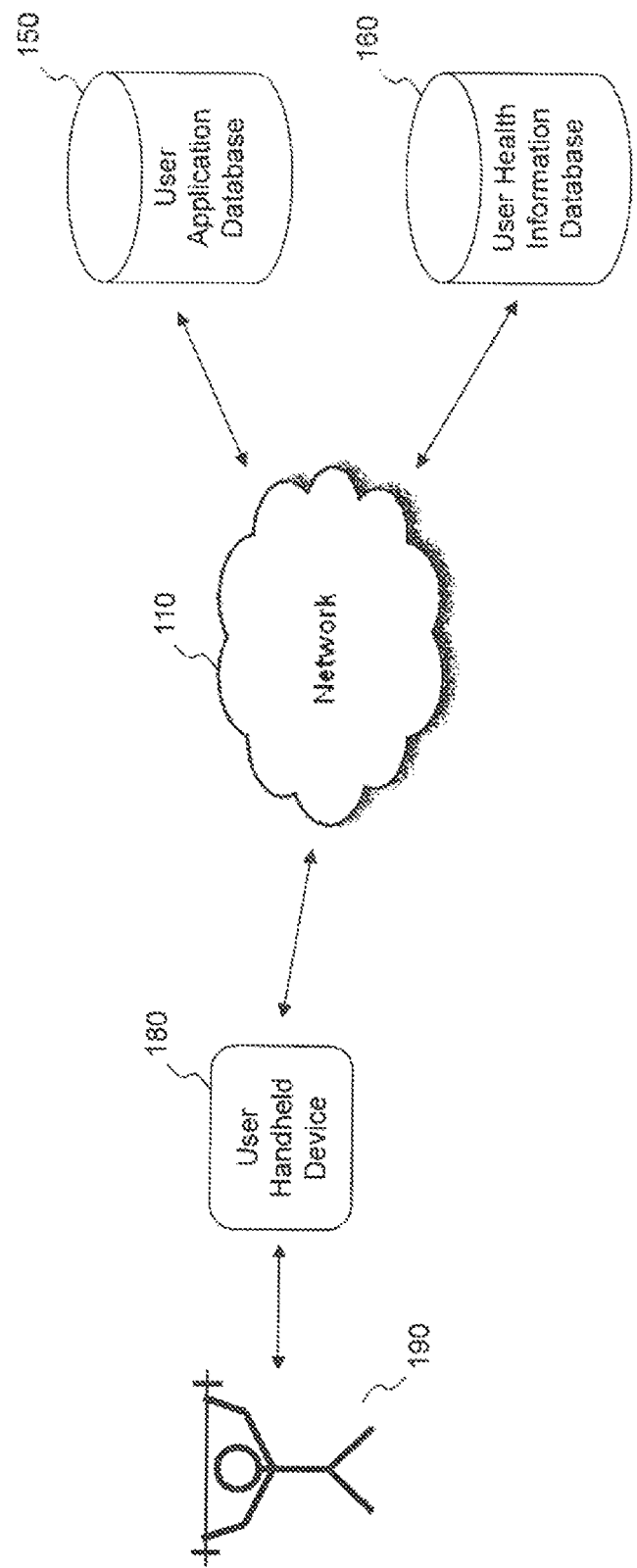
FIG. 1C is a block diagram depicting an embodiment of a user handheld device that can acquire user health data and communicate with a network.

FIG. 1C is a diagram illustrating a user handheld device 180 that can acquire user health and/or workout data and communicate with a network 110. User handheld device 180 can be any portable device, including, without limitation, a laptop, a PDA, a cell phone, a smart phone, a pager, a tablet, an iPod, a camera, or the like. For example, user 190 can be exercising while carrying user handheld device 180, wearing user handheld device 180, or otherwise being near user handheld device 180. In some embodiments, one or more sensor are attached to user 190 and the measurements captured by the one or more sensors can be accessible by user handheld device 180 such that user handheld device 180 can transmit the health and/or workout data (e.g., data derived from the measurements captured by the one or more sensors) to user health information database 160 for storage. In other embodiments, one or more sensors can be attached to or included within the user handheld device 180 (e.g., coupled to the surface of user handheld device 180 via an electrical or mechanical connection, embedded within user handheld device 180, etc.). For example, the user 190 can be wearing the user handheld device 180 and the one or more sensors attached to or included within the user handheld device 180 can be in contact with the user 190. Measurements captured by the one or more sensors can be transmitted to the user handheld device 180 and the user handheld device 180 can transmit the health and/or workout data (e.g., data derived from the measurements captured by the one or more sensors) to user health information database 160 for storage. Note that user handheld device 180 can transmit health and/or workout data even if user 190 is not exercising. User handheld device 180 can transmit health and/or workout data related to any activity user 100 may be engaging in, including when user 190 is eating or idle. In this way, all activities user 190 engages in can be monitored and stored for future use.

Figure 2:
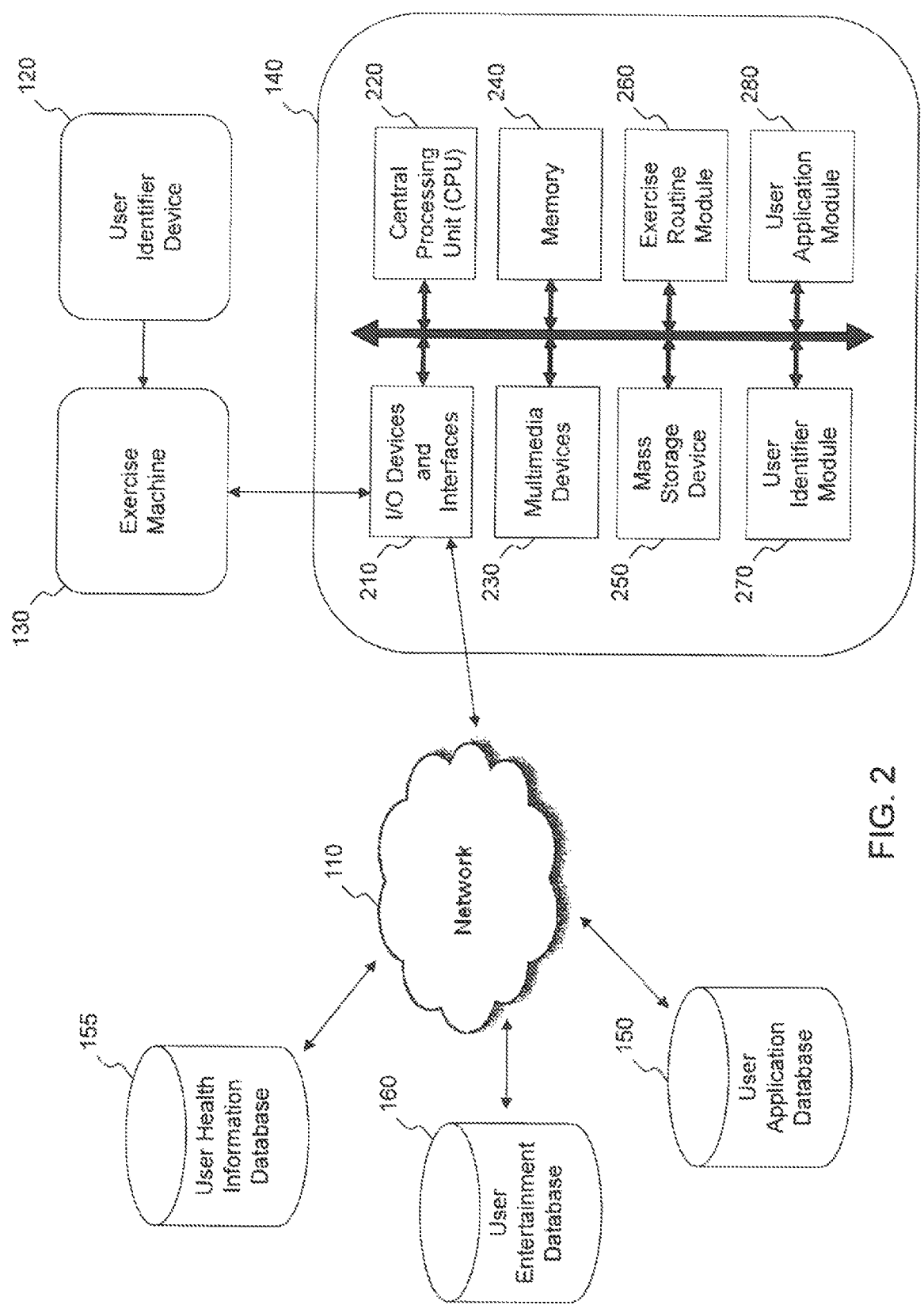
FIG. 2 is a block diagram depicting an embodiment of a more detailed network communication device.

FIG. 2 is a diagram illustrating a more detailed network communication device 140. Network communication device 140 includes an exercise routine module 260, user identifier module 270, and user application module 280, which carry out the functions, methods, and/or processes described herein. Exercise routine module 260, user identifier module 270, and user application module 280 are each executed on the network communication device 140 by a central processing unit 220 discussed further below.

In general the word "module," as used herein, refers to logic embodied in hardware or firmware or to a collection of software instructions, having entry and exit points. Modules are written in a program language, such as JAVA, JavaScript, HTML, XML, CSS, AJAX, PHP, C, C#, or C++, or the like. Software modules can be compiled or linked into an executable program, installed in a dynamic link library, or can be written in an interpreted language such as BASIC letters, ASP, PERL, LUA, PHP, Ruby, Python, or the like. Software modules can be called from other modules or from themselves, and/or can be involved in response to detected events or interruptions. Modules implemented in hardware include connected logic units such as gates and flip-flops, and/or can include programmable units, such as programmable gate arrays or processors.

Generally, the modules described herein refer to logical modules that can be combined with other modules or divided into sub-modules despite their physical organization or storage. The modules are executed by one or more computing systems, and can be stored on or within any suitable computer readable medium, or implemented in-whole or in-part within special designed hardware or firmware. Not all calculations, analysis, and/or optimization require the use of computer systems, though any of the above-described methods calculations, processes or analyses can be facilitated through the use of computers. Further, in some embodiments, process blocks described herein can be altered, rearranged, combined, and/or omitted.

Network communication device 140 includes one or more central processing units (CPU) 220, which can include a microprocessor. Network communication device 140 further includes a memory 240, such as random access memory (RAM) for temporary storage of information, a read only memory (ROM) for permanent storage of information, and a mass storage device 250, such as a hard drive, a flash drive, a memory card, a diskette, an optical media storage device, or the like. Alternatively, the mass storage device can be implemented in an array of servers. Typically, the components of the network communication device 140 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

Network communication device 140 includes one or more input/output (I/O) devices and interfaces 210, such as a keyboard, mouse, touchpad, and printer. The I/O devices and interfaces 210 can include one or more display devices, such as a monitor, that allows the visual presentation of data to a user. More particularly, a display device provides for the presentation of GUIs as application software data, and multi-media presentations, for example. The I/O devices and interfaces 210 can also provide a communications interface to various external devices. The network communication device 140 can include one or more multi-media devices 230, such as speakers, video cards, graphics accelerators, and microphones, for example.

Network communication device 140 can run on a variety of computing devices, such as a server, a virtual server, a Windows server, and Structure Query Language server, a Unix Server, a Linux Server, a Mac Server, a personal computer, a laptop computer, and so forth. In other embodiments, network communication device 140 can run on a mainframe computer suitable for controlling and/or communicating with large databases, performing high volume transaction processing, and generating reports from large databases. Network communication device 140 is generally controlled and coordinated by an operating system software, such as z/OS, Windows 95, Windows 98, Windows NT, Windows 2000, Windows XP, Window Vista, Windows 7, Linux, Unix, BSD, SunOS, Solaris, tinyOS, iOS, Windows Mobile, Android, webOS, or other compatible operating systems, including proprietary operating system. Operating systems control and schedule computer processes for execution, perform memory management, provide file system, networking, and I/O services, and provide a user interface, such as a graphical user interface (GUI), among other things.

Network communication device 140 is coupled to a network 110, such as a LAN, WAN, or the Internet via a communication link (wired, wireless, or a combination thereof). Network 110 communicates with various computing devices and/or other electronic devices. User application module 280 can access or can be accessed through a web-enabled user access point. Connections can be a direct physical connection, a virtual connection, and other connection type. The web-enabled user access point can include a browser module that uses text, graphics, audio, video, and other media to present data and to allow interaction with data via network 110. The browser module can display media associated with an application as well.

The browser module can also present advertisements based on identifiable or non-identifiable health and/or workout data captured by exercise machine 130 and/or stored in user health information database 155. Health and/or workout data captured by exercise machine 130 during the showing of a given advertisement can be relayed to the advertisers to provide feedback on the effectiveness or usefulness of an advertisement. For example, if a user's heart rate data spikes during the showing of a particular advertisement or if a user temporarily slow down during the showing of a particular advertisement, an advertiser can be notified that the advertisement may be pertinent to other individuals with similar health and/or workout data. Likewise, feedback on the effectiveness or usefulness of an advertisement can be transmitted for use in search engines. In this way, a user's health and/or workout data can be used to generate feedback on advertisements and, in conjunction with already accumulated user data, like web habits, can be used to produce more targeted and effective advertising. The same applies to e-commerce stores, where a user's health and/or workout data can be used to generate feedback on advertisements and, in conjunction with already accumulated user data, like spending habits, can be used to produce more targeted and effective advertising.

The browser module or other output module can be implemented as a combination of an all-points addressable display such as a cathode ray rube (CRT), a liquid crystal display (LCD), a plasma display, a field emission display (FED), a surface-conduction electron-emitter display (SED), a light-emitting diode display (LED), an organic light-emitting diode display (OLED), an active-matrix organic light-emitting diode display (AMOLED), or other types and/or combinations of displays. The output module can be implemented to communicate with input devices 210 and they also include software with the appropriate interfaces which allow a user to access data through the use of stylized screen elements, such as menus, windows, dialogue boxes, tool bars, and controls (e.g., radio buttons, check boxes, sliding scales, and so forth). Furthermore, the output module can communicate with a set of input and output devices to receive signals from the user.

In an embodiment, user identifier module 270 receives user identification data from user identifier device 120, either directly or indirectly through exercise machine 130, and generates a key that can be used to extract data from user application database 150, user health information database 155, and/or user entertainment database 160 that corresponds to the user in question.

User application module 280 can receive at least one application relating to the user from user application database 150. In some embodiments, user application module 280 can also contain pre-selected applications, designated by the gymnasium, manufacturer, or other third party. In further embodiments, user application module 280 can also receive entertainment data from user entertainment database 160. User application module 280 can execute the at least one application based on a user preference. For example, the user can select one or more applications to execute through the web-enabled user access point.

Applications can be any program that could be executed by the operating system software loaded in network communication device 140. In an embodiment, an application could generate an exercise regimen for the user based on health and/or workout data received from user health information database 155. Once executed, user application module 280 could instruct exercise routine module 260 to generate command signals to control how exercise machine 130 functions. For example, in situations in which exercise machine 130 is as aerobic machine, exercise routine module 260 could send command signals to exercise machine 130 to instruct it to simulate running on an incline by adjusting the tension and/or slope of exercise machine 130. Furthermore, an application can simulate an actual geographical route, like a trail in Yosemite, by instructing exercise routine module 260 to send command signals to exercise machine 130 such that the tension and/or slope is adjusted according to the layout of the actual geographical route.

In addition, an application could inform the user of the particular exercise it is recommending through the web-enabled user access point or other display device. For example, in situations in winch exercise machine 130 is a lifting machine, the web-enabled user access point or other display device could speak, display text, make a noise, vibrate, and/or flash a light to indicate to the user that he or she should do a certain number of reps or that the person has completed a particular set. If an application determines that the user should exercise on a different exercise machine, this information could be displayed or verbally spoken to the user through the web-enabled user access point as well.

In another embodiment, an application could play music or video based on entertainment data received from user entertainment database 160. In this way, a user would not need to bring his or her portable music and or video device, like a cell phone, smart phone, cassette player, optical disc player, music file player, video file player, or the like, to listen to his or her own music or watch his or her own videos.

Figure 3:
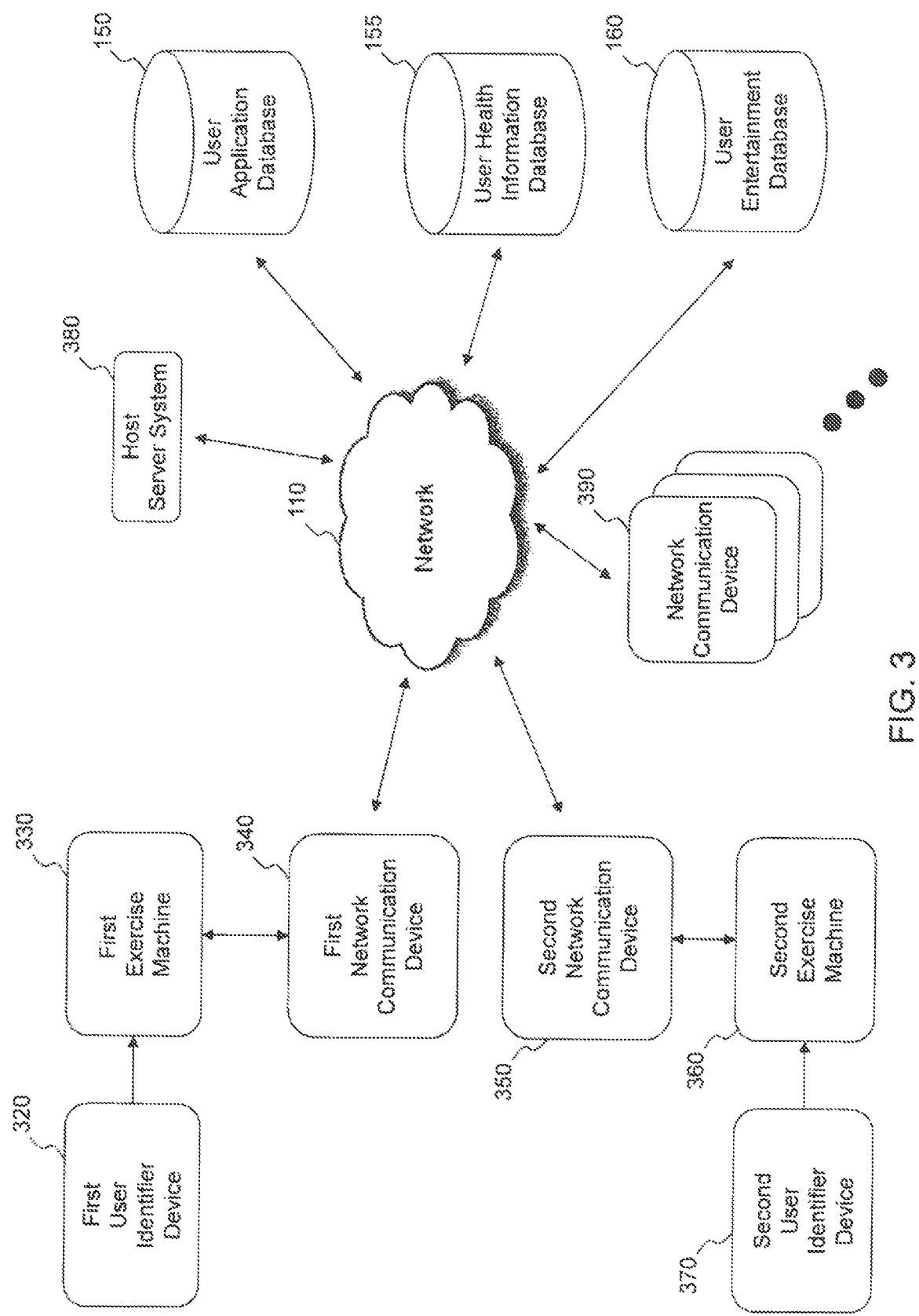
FIG. 3 is a block diagram depicting an embodiment of at least two network communication devices in communication with each other and with exercise machines.

FIG. 3 is a diagram illustrating at least two network communication devices 340, 350, and/or 390 that can interact with each other through network 110 and host server system 380. In an embodiment, at least two users can exercise together and compete in real-time. For example, the at least two network communication devices 340, 350, and/or 390 can all execute an identical application or applications. Alternatively, one of the at least two network communication devices 340, 350, and or 390 can execute an application. The network communication device 340, 350, or 390 that executes the application can then generate command signals to control each of the exercise machines 330 and 360 in communication with the at least two network communication devices 340, 350, and/or 390. Host server system 380 can serve as an intermediary device, establishing a forum in which users can find each other, hosting data related to each user's performance, and relaying such data to the other users. Each user can track his or her progress through the web-enabled user access point or other display device and compare his or her performance against the others also exercising at the same time. The application or applications executed by the at least two network communication devices 340, 350, and/or 390 can be any application that could be executed by the loaded operating system software. In this way, multiple users can exercise together even when geographically separated.

In another embodiment, at least two users can compete against one another even if they are not exercising together in real-time. Host server system 380 can store exercise information relating to a first user who exercised earlier than a second user. For example, host server system 380 can store the time it took for a first user to complete the exercise and/or how far the first user had run at a given point in time. When the second user begins his or her first exercise, he or she can view the first user's performance data in the web-enabled user access point or other display device. In this way, multiple users can exercise together even when their schedules dictate that they work out at different times of the day.

Note that while at least two users are competing and/or exercising with each other, each user's health and/or workout data can still be collected and stored in user health information database 160. Likewise, each user, by signing in via user identifier devices 320 and/or 370, can load and execute their own personal applications while exercising with others. For example, a user can load and execute an application that plays the user's music while racing against another user.

Host server system 380 can support any number of users. In this way, users can compete remotely in large-scale events, like a 10K race or a marathon.

Figure 4:
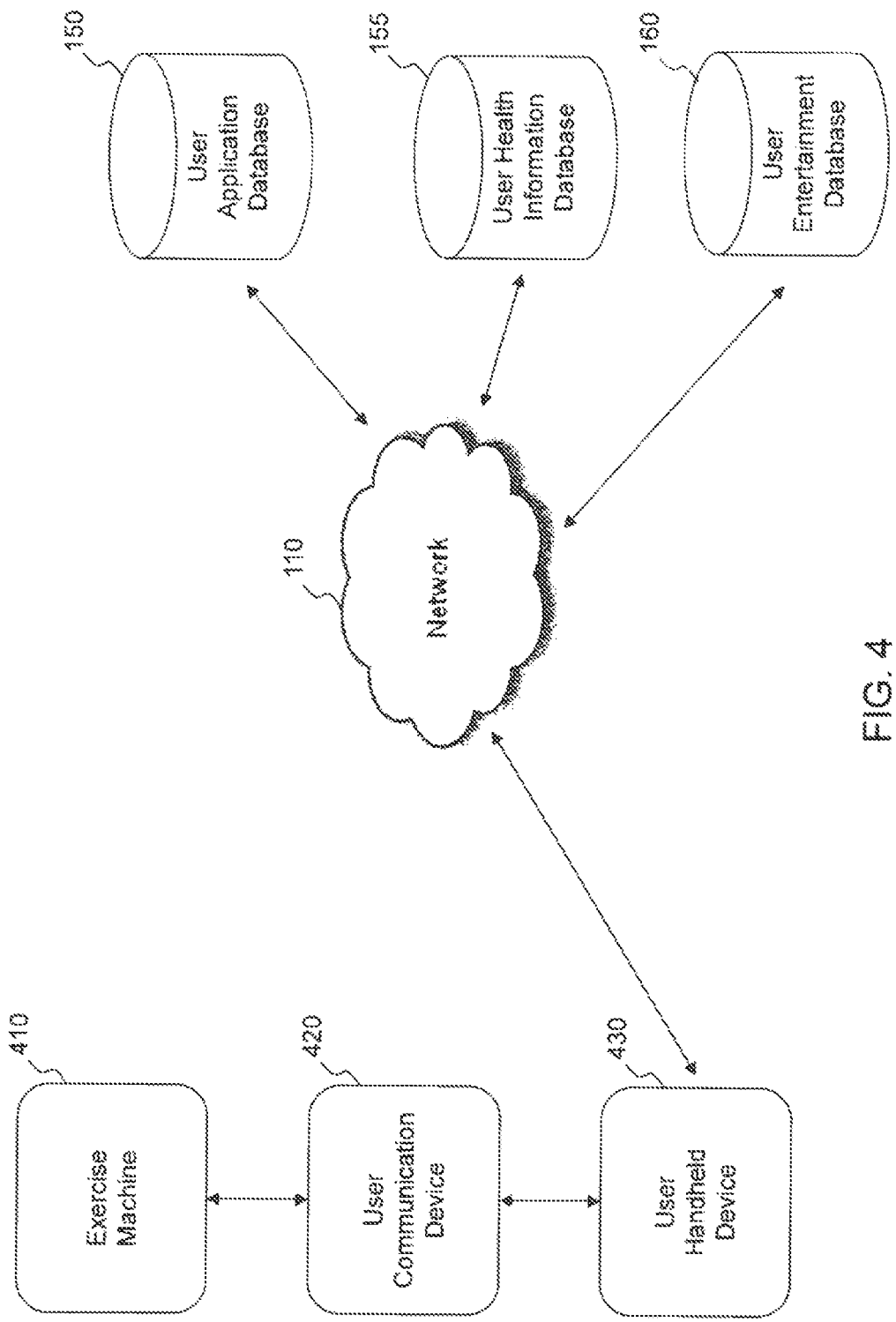
FIG. 4 is block diagram depicting an embodiment of a user handheld device in communication with a network and a user communication device.

FIG. 4 is a diagram illustrating user communication device 420 is similar to network communication device 140 as described above in FIGS. 1A, 1B, and 2. User communication device 420, however, does not communicate directly with network 110. Instead, user handheld device 430 serves as an intermediary between user communication device 420 and network 110. For example, if exercise machine 410 is not equipped with networking capabilities or it is otherwise impractical for exercise machine 410 to be in communication with network 110 in the gymnasium, user handheld device 430 can allow exercise machine 410 and user communication device 420 to communicate with network 110.

User handheld device 430 can be any device that can communicate with a network such as, without limitation, a cell phone, a smart phone, a PDA, a pager, a tablet, a laptop, a camera, a music and/or video player, a modem, a router, or the like. User handheld device 430 can communicate with user communication device 420 through wired or wireless communications. In an embodiment, user handheld device 430 can be physically docked to user communication device 420. User handheld device 430 can connect to user communication device 420 via Ethernet, USB 1.0, USB 2.0, USB 3.0, IEEE 1394, IEEE 1394a, IEEE 1394b, Thunderbolt, VGA, DVI, HDMI, optical fiber, serial port, parallel port, or the like. In other embodiments, user handheld device 430 can communicate with user communication device 420 wirelessly via Bluetooth, NFC technology, the 802.11 standard, the 802.15.4 standard, RFID or the like. Likewise, user handheld device 430 can communicate with network 110 through similar wired or wireless standards.

User handheld device 430 can retrieve data from user application database 150, user health information database 155, and/or user entertainment database 160 for use by user communication device 420. User communication device 420 can utility such data in the same way as network communication device 140 as described above with respect to FIGS. 1A, 1B, and 2. Likewise, user handheld device 430 can receive health and/or workout data from user communication device 420 and/or exercise machine 410 for storage in user health information database 155.

In an embodiment, a user identifier device 120, as described above with respect to FIGS. 1A, 1B, and 2, may not be necessary in order to uniquely identify an individual. A user using a personal user handheld device 430 can log in via user handheld device 430. In this way, even if a user is borrowing another person's user handheld device 430, the user can still retrieve and store his or her personal health and/or workout data. In other embodiments, a user identifier device similar to user identifier device 120 in FIGS. 1A, 1B, and 2 can be in communication with exercise machine 410. For example, some user handheld devices 430 may not have the means to allow a user to uniquely identify him or herself. A user identifier device similar to user identifier device 120 could be used to uniquely identify an individual, and user handheld device 430 could obtain this identity information to retrieve the appropriate data.

Figure 5:
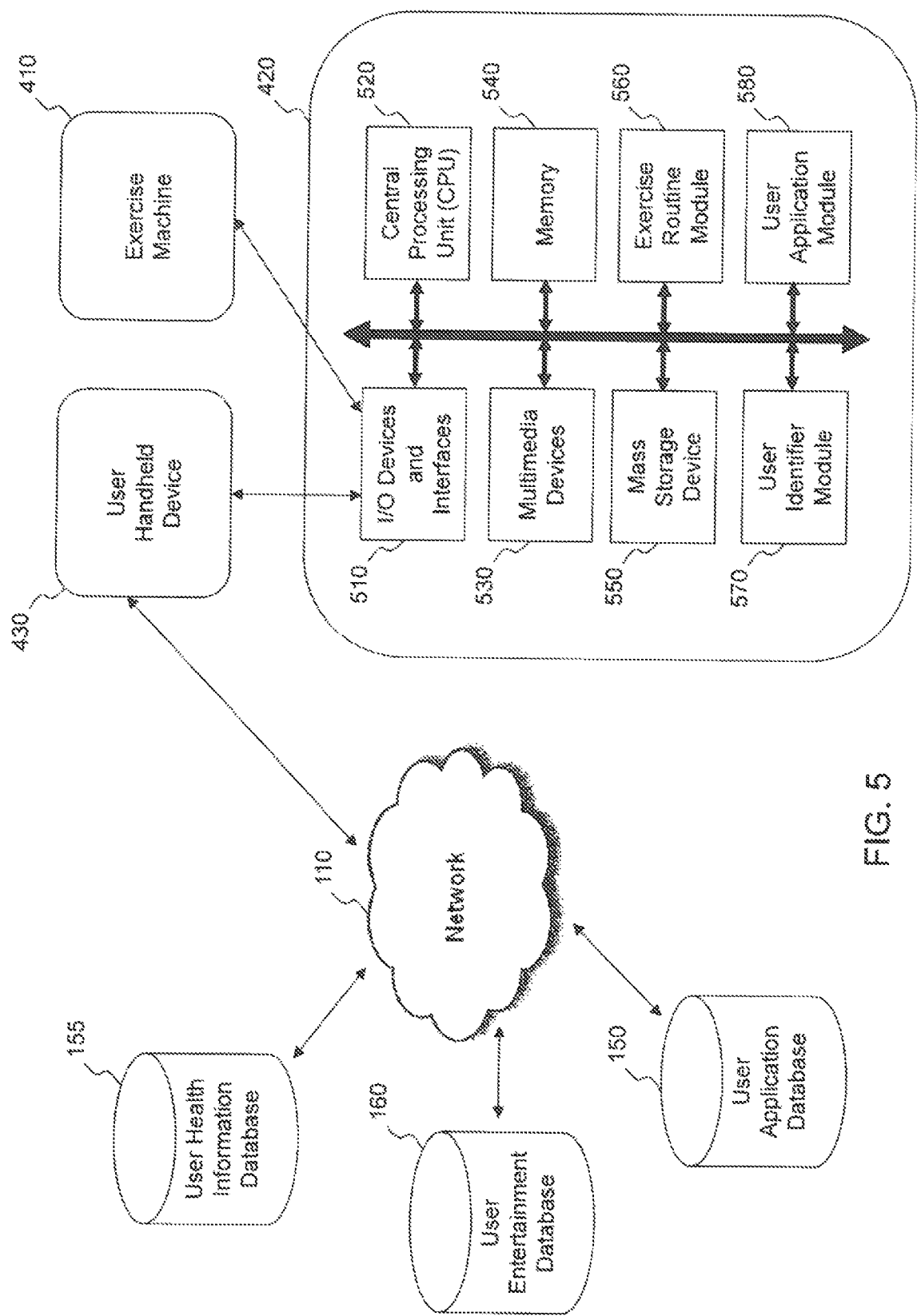
FIG. 5 is a block diagram depicting an embodiment of a more detailed user communication device.

FIG. 5 is a diagram illustrating a more detailed user communication device 420. User communication device 420 can include eight modules: I/O devices and interfaces 510, at least one central processing unit (CPU) 520, multimedia devices 530, memory 540, mass storage device 550, exercise routine module 560, user identifier module 570, and user application module 580. In an embodiment, these modules function as their similarly named counterparts in network communication device 140 and as described with respect to FIG. 2.

Figure 6:
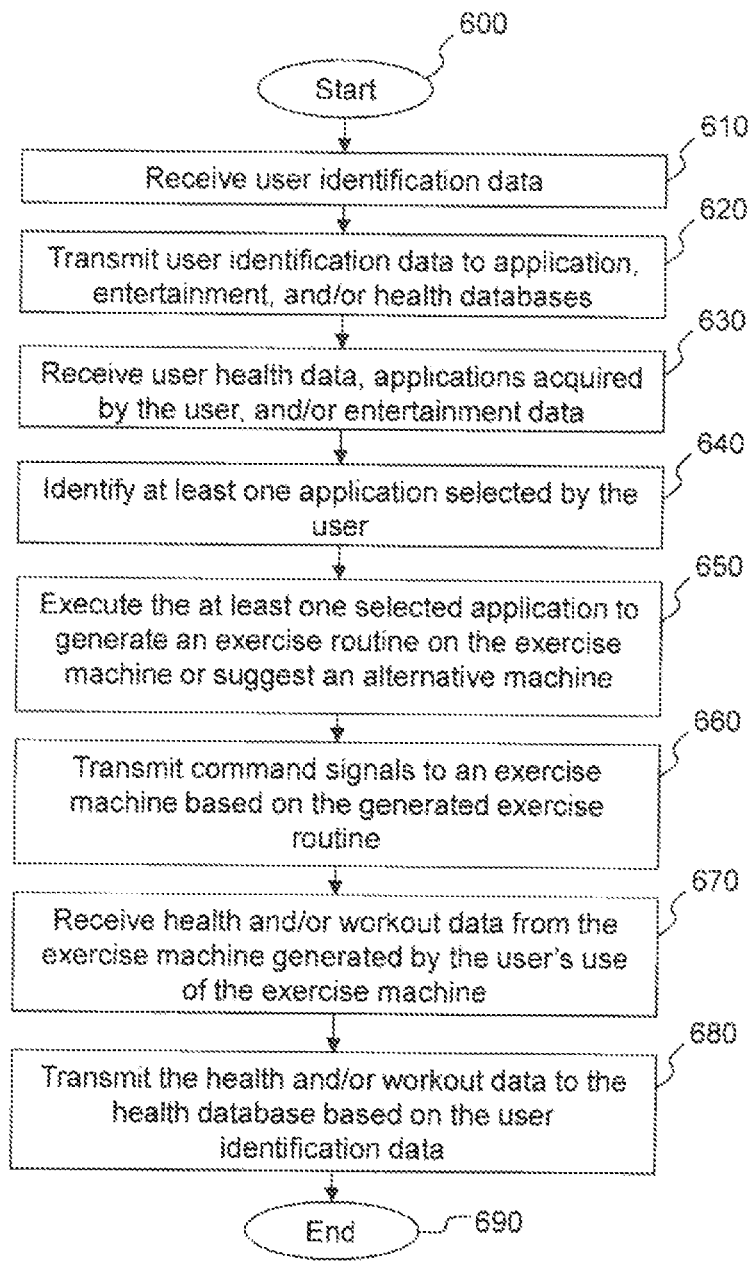
FIG. 6 is a flow chart depicting an embodiment of a process for loading and executing an application on an exercise machine to capture and store a user's health data.

FIG. 6 is a flowchart illustrating a process for loading and executing at least one application in network communication device 140 or user communication device 420. The process begins at block 610 with the process receiving user identification information from user identifier device 120 and/or exercise machine 130 as described above with respect to FIG. 1A. At block 620, the process transmits the user identification data to user application database 150, user health information database 155, and/or user entertainment database 160. In some embodiments, the process can generate a key or other database query code based on the user identification data. This key or code can be sent to all or some of the three databases to retrieve the requested data. At block 630, the process receives health and/or workout data, entertainment data, and/or application data from some or all of the three databases.

At block 640, the process identifies at least one application selected by the user. In an embodiment, the user can select an application using the web-enabled user access point or other display device as described herein. In some embodiments, the at least one application can be an application pro-selected by the gymnasium or manufacturer of exercise machine 130 and stored in network communication device 140. In other embodiments, the at least one application can be an application acquired by the user and stored in user application database 150.

At block 650, the process executes the at least one selected application to generate an exercise routine for the user on the exercise machine the user is currently operating. In addition, the execution can result in the generation of command signals to control operation of the exercise machine. In some embodiments, the execution can generate a message instructing the user to exercise on a different machine and provide an exercise routine for the different machine.

At block 660, the process transmits the generated command signals to an exercise machine being used by the user. As described herein, for example, the command signals can adjust the tension and/or slope of the exercise machine.

At block 670, the process receives health and/or workout data from exercise machine 130 generated by the user's exercising. As described herein, received health and/or workout data can include, without limitation, the number of reps done, the number of sets completed, the time taken between reps, the time taken between sets, the amount of weight lifted, distance run, speed, number of calories burned heart rate, wattage produced, exercise equipment used, which exercise equipment is used the most, which exercise equipment is used the least, the time of day the workout took place, the time of the year the workout took place, preexisting conditions, prior injuries, muscle gained, fat lost, or the like.

At block 680, the process transmits the received health and/or workout data to user health information database 155. The process can automatically enter the data into the correct field based on a key or code generated from the user identification data, or based on the user identification data itself. At block 690 the process ends.

Figure 7:
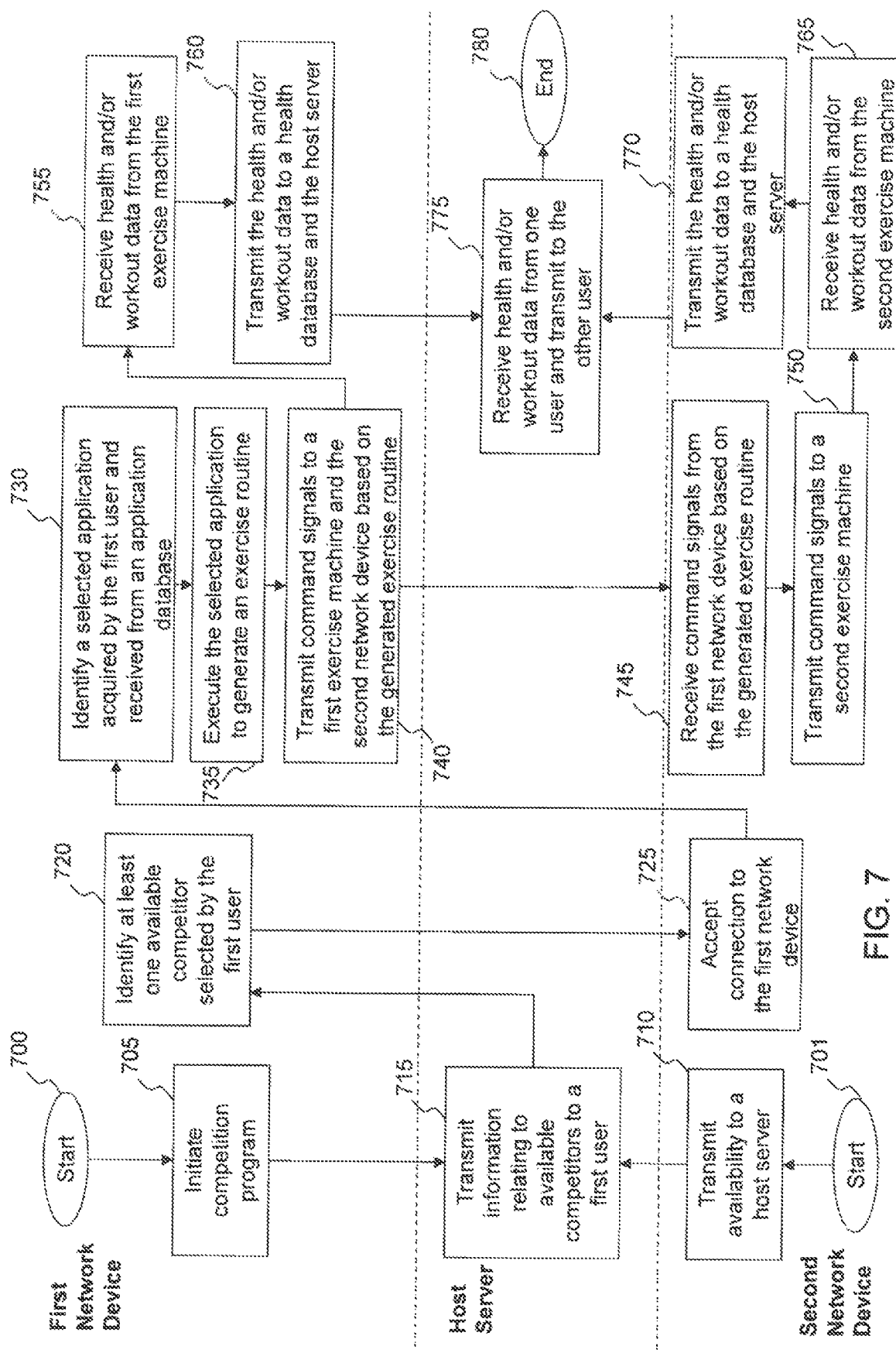
FIG. 7 is a flow chart depicting an embodiment of a process for loading and executing at least one application on at least two exercise machines to allow at least two users to exercise and/or compete with each other.

FIG. 7 is a flowchart illustrating a process for loading and executing at least one application on at least two exercise machines to allow at least two users to exercise and/or compete with each other. The process begins at block 705 and at block 710. At block 705, the process initiates a competition program. The process occurs at a first network device, which can be similar to network communication device 140 or user communication device 420 as described above with respect to FIGS. 1A, 1B, 2, and 4. In some embodiments, the competition program can be obtained from user application database 150. In other embodiments, the competition program can be pre-stored in network communication device 140 or user communication device 420.

At block 710, the process, at a second network device, transmits its availability to a host server, indicating that a second user is available to connect to others. Like with the first network device, the second network device can be similar to network communication device 140 or user communication device 420. The host server can be similar to host server system 380 as described above with respect to FIG. 3. Alternatively, not shown, the process can initiate the same competition program at the second network device as at the first network device. This can allow the process to later visualize the performance of each user in a uniform display viewable by both users.

At block 715, the process, at the host server, transmits information relating to available competitors to the first user through the first network device. Note that the host server and the first network device and the host server and the second network device can be in communication with each other through a network, like network 110 as described with respect to FIGS. 1A-C and 2-5. Accordingly, the host server is not limited in the number of users it can identify as being available.

At block 720, the process, at the first network device, identifies at least one competition selected by the first user. The first user can select one or more competitors through the web-enabled user access point, as described herein.

At block 725, the process, at the second network device, accepts a connection to the first network device. When the first user selects more than one available competitor, the process, at each addition network device, could accept a connection to the first network device.

At block 730, the process, at the first network device, identifies at least one selected application acquired by the first user and received from the user application database 150. Alternatively, not shown, the process can identity at least one application selected by the first user that was already pre-loaded at the first network device.

At block 735, the process, at the first network device, executes the at least one selected application to generate an exercise routine. The exercise routine can be based on the first user's health and/or workout data acquired from user health information database 155. Alternatively, not shown, the process, at both the first network device and the second network device, can execute the same application. Again, this can allow the process to later visualize the performance of each user in a uniform display view able by both users.

At block 740, the process, at the first network device, transmits command signals to a first exercise machine and the second network device based on tire generated exercise routine. Note that even if the process executes the application at the second network device, the process can still transmit the command signals to the second network device to ensure that both users are competing on an equal playing field.

At block 745, the process, at the second network device, receives command signals from the first network device based on the generated exercise routine. At block 750, the process, at the second network device, transmits these command signals to a second exercise machine. As described herein, the command signals can adjust the tension and/or slope of the second exercise machine.

At block 755, the process, at the first network device, receives health and/or workout data from the first exercise machine. At block 760, the process, at the first network device, transmits the received health and/or workout data to the user health information database 155 and/or the host server. In some embodiments, the host server may only receive data that is sufficient for each user to compare their progress against the other.

At block 765, the process, at the second network device, receives health and/or workout data from the second exercise machine. At block 770, the process, at the second network device, transmits the received health and/or workout data to the user health information database 155 and/or the host server. In some embodiments, the host server may only receive data that is sufficient for each user to compare their progress against the other.

At block 775, the process, at the host server, receives health and/or workout data from each user and transmits the same to the other user. In addition, not shown, the process can display performance data at the first network device and the second network device. The performance data can be based on the health and/or workout data received by the host server. At block 780, the process ends.

In other embodiments not shown, at least two users can compete against each other at different times. For example, in this instance, the process would not need to initiate contact between the first network device and the second network device. A user at the first network device could complete his or her workout and the process could transmit the workout information and any exercise machine command signals to the host server. When a second user wishes to compete against a first user that has already completed his or her exercise, the process could transmit the workout information and any exercise machine command signals to the second network device. In this way, the second user could participate in the same exercise routine as the first user and compare his or her performance.

Figure 8:
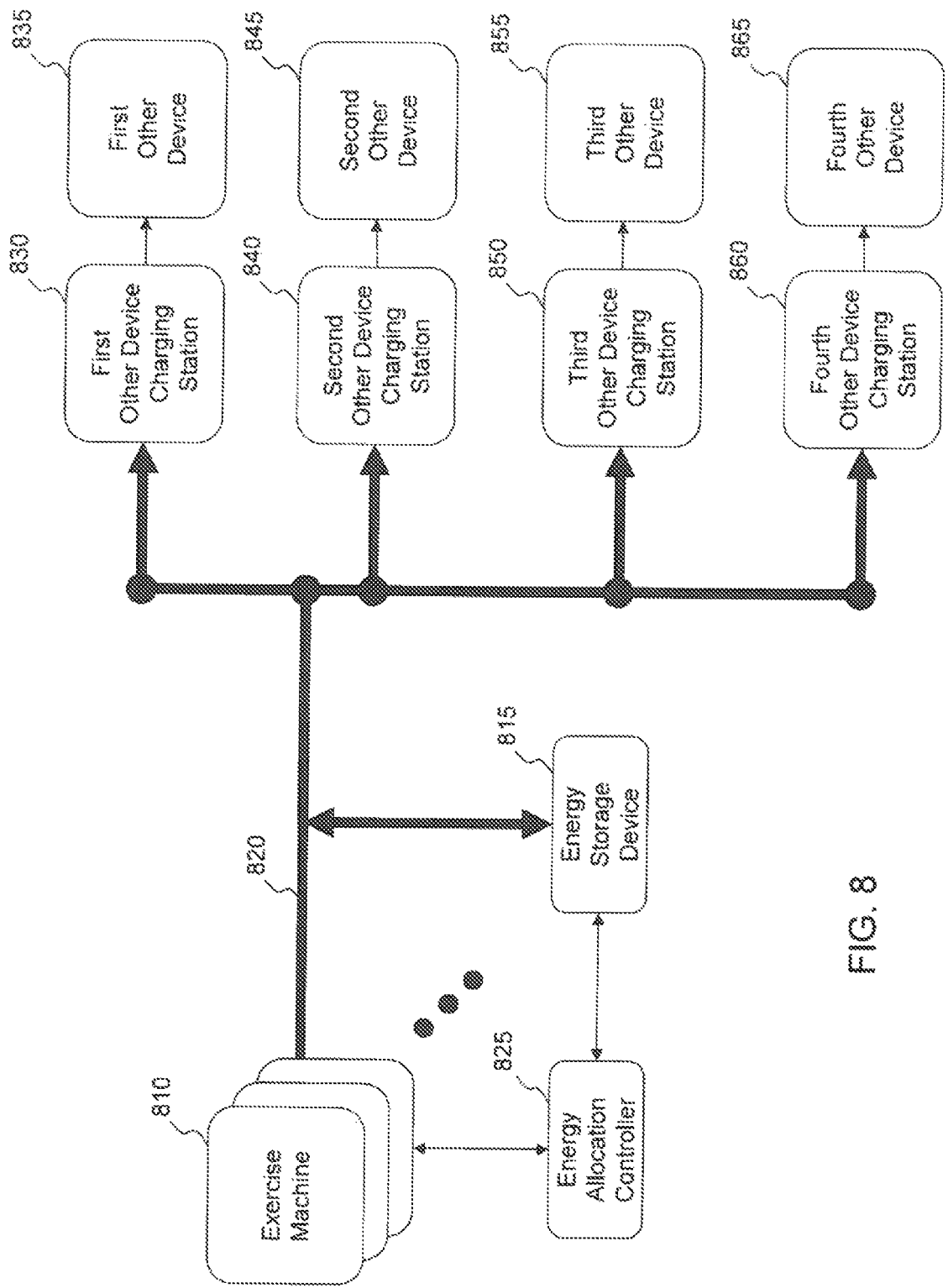
FIG. 8 is a block diagram depicting an embodiment of a device charging system.

FIG. 8 is a diagram illustrating a system to power and/or charge hybrid and/or electric automobiles airplanes, motor boats, motorcycles, scooters, or other like motor vehicles. Exercise machines 810 can be located in a gymnasium or other such establishment. While exercise machines 810 are in use electrical energy can be generated. This electrical energy can be stared in storage device 815 for future use via transmission along transmission bus 820. Energy storage device 815 can be a capacitor or a rechargeable battery, such as, without limitation, lead acid, lithium ion, lithium ion polymer, nickel cadmium, nickel metal hydride, or reusable alkaline. Transmission bus 820 can be any type of line that can carry electrical current including, without limitation, a coaxial cable, a microstrip, a stripline, a balanced line, a twisted pair, a star quad, a twin-lead, a lecher line, a single-wire line, a waveguide, an optical fiber, or the like.

In some embodiments, the electrical energy can be transmitted along transmission bus 820 to other device charging stations 830, 840, 850, and/or 860. Other devices 835, 845, 855, and/or 865 can be coupled to any of other device charging stations 830, 840, 850, and/or 860. Other devices 835, 845, 855, and/or 865 and other device charging stations 830, 840, 850, and/or 860 can be coupled wirelessly or through wired communications. For example, without limitation, the connection can be inductive or through a cable like USB or IEEE 1394.

Other device charging stations 830, 840, 850, and/or 860 can be equipped to charge hybrid and/or electric motor vehicles, such as automobiles, airplanes, motor boats, motorcycles, scooters, or the like. In addition, other device charging stations 830, 840, 850, and/or 860 can be equipped to charge personal devices, such as cell phones, smart phones, PDAs, pagers, tablets, cameras, music and/or video players, laptops, or the like. Other device charging stations 830, 840, 850, and/or 860 can be located near a gymnasium or other establishment such that they can draw electrical energy from users exercising on exercising machines 810.

When none of other device charging stations 830, 840, 850, and/or 860 are in use, electrical energy that is generated can be stored in energy storage device 815. Likewise, when none of exercise machines 810 are in use, other device charging stations 830, 840, 850, and/or 860 can draw electrical energy from energy storage device 815 in order to charge other devices 835, 845, 855, and/or 865. Note that this embodiment is not limited to four charging stations or four other devices, nor does it require that at least four charging stations be built.

In an embodiment, the amount of electrical energy available to charge an other device 835, 845, 855, or 865 can depend on the amount of exercise completed by a user associated with the other device 835, 845, 855, and/or 865. For example, when initially docking his or her other device 835, 845, 855, and/or 865 for charging, a user can sign in to other device charging station 830, 840, 850, and/or 860. A user can sign in using a module similar to user identifier device 120 described herein with respect to FIGS. 1A, 1B, and 2. Likewise, a user can then subsequently sign in to an exercise machine 810 using a module similar to user identifier device 120 described herein with respect to FIGS. 1A, 1B, and 2. By signing in, the system can associate a particular exercise machine 810 a user is operating with the other device charging station 830, 840, 850, and/or 860 that the user's other device 835, 845, 855, and/or 865 is docked at. Each exercise machine 810 can track the amount of wattage generated by the user operating it and transmit this data to energy allocation controller 825.

Energy allocation controller 825 can be any device that can control the output of energy storage device 815. Energy allocation controller 825 can tally the total amount of wattage generated by all exercise machines 810 and then assign a percentage value to each user based on the amount of energy each user contributed to the total. Energy allocation controller 825 can then direct energy storage device 815 to distribute a percentage of its total stored energy to the other device charging station 830, 840, 850, and/or 860 associated with the user, where the distributed percentage is based on the percentage value assigned to the user.

In other embodiments, not shown, the electrical energy produced can be used to power the gymnasium or other such establishment itself. The amount of energy generated by a particular user could be tracked by exercise machine 810 and/or energy allocation controller 825, such that the user's membership dues are reduced proportionally or directly by the cost of energy he or she produced. Transmission bus 820 can also be coupled with the main power grid, and the electrical energy could be sold back to the utility company.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. Thus, it is intended that the scope of the present invention herein disclosed should not be limited by the particular disclosed embodiments described above.

Conditional language, such as, among others, "can," "could," "might," or "may," unless specifically stated otherwise, or otherwise understood within the context as used, is generally intended to convey that certain embodiments include while other embodiments do not include, certain features, elements and/or blocks. Thus, such conditional language is not generally intended to imply that features, elements and/or blocks are in any way required for one or more embodiments or that one or more embodiments necessarily include logic for deciding, with or without user input or prompting, whether these features, elements and/or steps are included or are to be performed in any particular embodiment.

What is claimed is:

1. A system comprising:
   a network device configured to establish wired or wireless communications over a network; and an exercise machine comprising:
- a non-transitory memory configured to store computer-executable instructions; and
- a processor that executes the computer-executable instructions to at least:
  - receive user identifying information input into the exercise machine to log a user into the exercise machine to uniquely identify the user, the user identifying information being associated with the user to record and store the user's workout data;
  - receive, via the network device, data associated with an exercise routine for the user from a database;
  - visually display the data associated with the exercise routine to the user on a visual display interface associated with the exercise machine;
  - inform the user of a particular suggested exercise via the visual display interface, wherein the particular suggested exercise is within the exercise routine;
  - access, via the network device, a host server system comprising workout data of a plurality of other users selected based on the exercise routine;
  - retrieve, via the host server system and the network device, workout data of at least one of the plurality of other users, wherein the at least one of the plurality of other users is performing or has previously performed the exercise routine;
  - display, via the visual display interface, the workout data of the at least one of the plurality of other users to the user;
  - receive workout data of the user recorded by at least one sensor when the user engages in the exercise routine;
  - display the workout data of the user on the visual display interface as the workout data of the user is received, wherein the workout data of the at least one of the plurality of other users and the workout data of the user are displayed concurrently in a comparative uniform display, and wherein the workout data of the at least one of the plurality of other users and the workout data of the user each comprise an energy level produced during the exercise routine; and
  - display on the visual display interface a recommendation to the user to exercise using at least one different exercise machine.

2. The system of claim 1, wherein the at least one sensor comprises a sensor that is a part of the exercise machine and a sensor that is wearable by the user.

3. The system of claim 1, wherein the processor further executes the computer-executable instructions to retrieve the recommendation through the network device.

4. The system of claim 1, wherein the at least one of the plurality of other users is located at a remote distance from the exercise machine.

5. The system of claim 1, wherein the workout data further comprises an age of the user and a geographical location of the user, and wherein the workout data of the at least one of the plurality of other users further comprises an age of the at least one of the plurality of other users and a geographical location of at least one of the plurality of other users.

6. The system of claim 1, wherein the exercise machine and the at least one different exercise machine are each independently at least one of: a treadmill, an elliptical, an exercise bicycle, a bench press, one or more medicine balls, one or more dumbbells, one or more free weights, or a controlled weight machine.

7. The system of claim 1, wherein the instructions further comprise:
   - transmit the workout data of the user to the host server system for storage, where the workout data of the user in the host server system is available to any of the other users performing the exercise routine, wherein the workout data of the user is stored by time or date the particular exercise was performed; and wherein the display of the workout data is configured to allow the user to track the user's personal exercise performance over time.

8. The system of claim 1, wherein the processor further executes the computer-executable instructions to:
   - retrieve, via the network device, entertainment data from the database; and
   - display, via the visual display interface, the entertainment data for the user of the exercise machine, wherein the entertainment data comprises at least one of: music or video content.

9. A method comprising:
   - receiving, by a system comprising a processor, user identifying information input into an exercise machine associated with the system to log a user into the exercise machine to uniquely identify the user, the user identifying information being associated with the user to record and store the user's workout data;
   - receiving, by the processor via a network device associated with the exercise machine, data associated with an exercise routine for the user from a database;
   - visually displaying, by the processor, the data associated with the exercise routine to the user on a visual display interface associated with the system;
   - informing the user of a particular suggested exercise via the visual display interface, wherein the particular suggested exercise is within the exercise routine;
   - accessing, by the processor via the network device, a host server system comprising workout data of a plurality of other users selected based on the exercise routine;
   - retrieving, by the processor via the host server system and the network device, workout data of at least one of the plurality of other users, wherein the at least one of the plurality of other users is performing or has previously performed the exercise routine;
   - displaying, by the processor, the workout data of the at least one of the plurality of other users to the user on the visual display interface;
   - receiving, by the processor via the network device, workout data of the user recorded by at least one sensor when the user engages in the exercise routine;
   - displaying, by the processor, the workout data of the user on the visual display interface as the workout data of the user is received, wherein the workout data of the at least one of the plurality of other users and the workout data of the user are displayed concurrently in a comparative uniform display, and wherein the workout data of the at least one of the plurality of other users and the workout data of the user each comprise an energy level produced during the exercise routine; and
   - displaying on the visual display interface a recommendation to the user to exercise using at least one different exercise machine.

10. The method of claim 9, wherein the at least one of the plurality of other users and the user are at geographically distinct locations that are identified to each of the user and the at least one of the plurality of other users.

11. The method of claim 9, further comprising:
retrieving, by the processor, the recommendation through the network device.

12. The method of claim 9, wherein the at least one of the plurality of other users comprises a stored version of the user, wherein the stored version of the user comprises workout data of the user stored by the host server during a previous performance of the exercise routine.

13. The method of claim 9, wherein at least one of the other users comprises a user exercising at a previous time who is one of the plurality of other users.

14. The method of claim 9, wherein the exercise machine and the at least one different exercise machine are each at least one of: a treadmill, an elliptical, an exercise bicycle, a bench press, one or more medicine balls, one or more dumbbells, one or more free weights, or a controlled weight machine.

15. The method of claim 9, further comprising:
informing the user, by the processor via the visual display interface, that the user should complete a certain number of repetitions of the particular suggested exercise and that the user has completed the particular suggested exercise.

16. The method of claim 9, wherein the informing comprises indicating to the user with at least one of a visual, an audio, or a tactile signal.

17. A system comprising:
a user identifier device configured to receive log in information from a user and uniquely identify the user based on the log in information;
a network communication device configured to generate a key for the user based on the log in information and to communicate via a network with at least one database;
an exercise machine comprising:
a non-transitory memory configured to store computer-executable instructions; and
a processor that executes the computer-executable instructions to at least:
receive a selection of an exercise routine;
display information related to competitors at different geographic locations received from a host server based on the selection;
display a first exercise of the exercise routine;
record user health and/or workout data during the first exercise using sensors associated with the exercise machine, wherein the user health and/or workout data comprises user energy produced;
receive health and/or workout data associated with a competitor during the first exercise, wherein the competitor health and/or workout data comprises competitor energy produced, wherein the competitor completes the first exercise at a different time than the user;
display the user energy produced and the competitor energy produced during the first exercise being performed by the user; and
after completion of the first exercise by the user, provide a prompt suggesting that the user perform another exercise with a different exercise machine.

18. The system of claim 17, wherein the user energy produced and the competitor energy produced are based on a wattage produced by the user and the competitor.

* * * * *